US012657732B2

(12) United States Patent
Taki

(10) Patent No.: US 12,657,732 B2
(45) Date of Patent: Jun. 16, 2026

(54) RADIATION IMAGE PROCESSING APPARATUS, OPERATION METHOD OF RADIATION IMAGE PROCESSING APPARATUS, AND NON-TRANSITORY COMPUTER READABLE MEDIUM

(71) Applicant: FUJIFILM Corporation, Tokyo (JP)

(72) Inventor: Tomoko Taki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 273 days.

(21) Appl. No.: 18/350,542

(22) Filed: Jul. 11, 2023

(65) Prior Publication Data

US 2024/0020849 A1 Jan. 18, 2024

(30) Foreign Application Priority Data

Jul. 13, 2022 (JP) ................................. 2022-112598

(51) Int. Cl.
*G06T 7/174* (2017.01)
*G06T 5/00* (2024.01)
(Continued)

(52) U.S. Cl.
CPC ................ *G06T 7/174* (2017.01); *G06T 5/00* (2013.01); *G06T 7/0012* (2013.01); *G16H 30/40* (2018.01);
(Continued)

(58) Field of Classification Search
None
See application file for complete search history.

(56) References Cited

U.S. PATENT DOCUMENTS

| | | |
|---|---|---|
| 5,049,748 A | 9/1991 | Ito et al. |
| 2002/0090125 A1 | 7/2002 | Murakami |

(Continued)

FOREIGN PATENT DOCUMENTS

| | | |
|---|---|---|
| JP | H03-133277 A | 6/1991 |
| JP | 2002-165131 A | 6/2002 |

(Continued)

OTHER PUBLICATIONS

Demehri, S., et al. "Assessment of image quality in soft tissue and bone visualization tasks for a dedicated extremity cone-beam CT system." European radiology 25 (2015): 1742-1751. (Year: 2015).*

(Continued)

*Primary Examiner* — Matthew C Bella
(74) *Attorney, Agent, or Firm* — Studebaker Brackett PLLC

(57) ABSTRACT

A radiation image processing apparatus generates a first emphasis image by performing first emphasis processing on two radiation images, which are different from each other, in which a specific subject is imaged, generates a second emphasis image by performing second emphasis processing using at least any radiation image of the two radiation images, and generates correlation information between the first emphasis image and the second emphasis image. The radiation image processing apparatus displays the first emphasis image, a level value corresponding to a value of a first parameter, and an image quality indicator in which a difference between the first emphasis image and the second emphasis image is quantified, and receives a change of the level value.

16 Claims, 13 Drawing Sheets

(51) Int. Cl.
    G06T 7/00          (2017.01)
    G16H 30/40      (2018.01)

(52) U.S. Cl.
    CPC .............. *G06T 2207/20224* (2013.01); *G06T 2207/30168* (2013.01)

(56)           References Cited

U.S. PATENT DOCUMENTS

| | | | |
|---|---|---|---|
| 2020/0184634 A1 * | 6/2020 | McLeod | .............. G06T 7/0012 |
| 2021/0113171 A1 | 4/2021 | Taki | |

FOREIGN PATENT DOCUMENTS

| | | | | |
|---|---|---|---|---|
| JP | 2002-209142 A | 7/2002 | | |
| JP | 2011-250969 A | 12/2011 | | |
| JP | 2021-065317 A | 4/2021 | | |
| WO | WO-9423647 A1 * | 10/1994 | ............. | A61B 6/501 |

OTHER PUBLICATIONS

An Office Action, "Notice of Reasons for Refusal," mailed by the Japanese Patent Office on Mar. 31, 2026, which corresponds to Japanese Patent Application No. 2022-112598 and is related to U.S. Appl. No. 18/350,542; with English language translation.

\* cited by examiner

1

RADIATION IMAGE PROCESSING APPARATUS, OPERATION METHOD OF RADIATION IMAGE PROCESSING APPARATUS, AND NON-TRANSITORY COMPUTER READABLE MEDIUM

CROSS-REFERENCE TO RELATED APPLICATIONS

This application claims priority under 35 U.S.C § 119(a) to Japanese Patent Application No. 2022-112598 filed on 13 Jul. 2022. The above application is hereby expressly incorporated by reference, in its entirety, into the present application.

BACKGROUND OF THE INVENTION

1. Field of the Invention

The present invention relates to a radiation image processing apparatus, an operation method of a radiation image processing apparatus, and a non-transitory computer readable medium that provide an energy subtraction function.

2. Description of the Related Art

In the medical field, a radiography apparatus that images a subject by using radiation, such as X-rays, has been widespread. For example, in a case in which the subject is a person or an animal, a radiation image captured by using the radiography apparatus is used for diagnosis, treatment, or the like. In recent years, the radiation image used for diagnosis or the like is not limited to a so-called projection image, and various images obtained by processing the projection image are also used. For example, images showing a specific structure or tissue of the subject, such as a bone part image displaying a bone part of the subject, a soft part image displaying a soft tissue of the subject, and a blood vessel image displaying a blood vessel, are also used.

The bone part image and the soft part image can be generated by so-called subtraction processing. The subtraction processing is processing of calculating a difference by weighting at least two types of radiation images in which the energy of the radiation used for imaging is different, and is processing utilizing the fact that an attenuation coefficient of the radiation is different depending on a composition of the subject. As for the subtraction processing, a method and a system of energy subtraction performed at a low cost by using a general-purpose personal computer (PC) are known (JP2002-165131A).

SUMMARY OF THE INVENTION

As for processing image generated by, for example, the subtraction processing using the captured radiation image, in many cases, in order to obtain a good image quality for appropriately displaying a target structure, tissue, or the like, a radiologist or the like checks the image quality and the like of the radiation image used for the subtraction processing, and further, check of the image quality and the like and adjustment of the image quality of the generated processing image are performed. Therefore, in a case in which it is required to perform the subtraction processing a large number of times on a large number of radiation images by a medical examination or the like, a large amount of time and labor of the radiologist is required.

The present invention is to provide a radiation image processing apparatus, an operation method of a radiation image processing apparatus, and a non-transitory computer readable medium capable of easily and quickly generating a subtraction processing image in which an image quality is quantified and then adjusted.

An aspect of the present invention relates to a radiation image processing apparatus comprising a processor. The processor acquires two radiation images in which a specific subject is imaged by respectively using two types of radiation energies different from each other, generates a first emphasis image by performing first emphasis processing on the two radiation images using an arithmetic expression including a first parameter, generates a second emphasis image by performing second emphasis processing using at least any radiation image of the two radiation images, generates correlation information indicating a correlation between the first emphasis image and the second emphasis image, performs control of displaying, on a display unit, the first emphasis image, a level value corresponding to a value of the first parameter, and an image quality indicator indicating a degree of difference between the first emphasis image and the second emphasis image, which is quantified based on the correlation information, and receives a change of the level value.

It is preferable that the processor updates the value of the first parameter in a case in which the change of the level value is received, generates the first emphasis image by using the updated value of the first parameter, and displays, on the display unit, the level value updated corresponding to the updated value of the first parameter.

It is preferable that the processor performs control of displaying, on the display unit, a user interface that receives the change of the level value by a user.

It is preferable that, in the radiation image, a scattered ray component estimated according to a body thickness of the subject is removed for each pixel.

It is preferable that the first emphasis processing is subtraction processing.

It is preferable that the subject includes a bone part and a soft part, and the first emphasis image is a bone part image, and the second emphasis image is a soft part image.

It is preferable that the subject includes a bone part and a soft part, and the first emphasis image is a soft part image, and the second emphasis image is a bone part image.

It is preferable that the first emphasis processing includes processing of weighting one radiation image of the two radiation images by using the first parameter, and then subtracting the weighted radiation image from the other radiation image.

It is preferable that the second emphasis processing includes processing of weighting one radiation image of the two radiation images by using a second parameter, and then subtracting the weighted radiation image from the other radiation image.

It is preferable that the subject includes a bone part and a soft part, the first emphasis image is a bone part image, and the second emphasis image is a soft part image, and in a case in which a pixel value at coordinates (x, y) in one radiation image of the two radiation images is $G1(x, y)$, a pixel value at coordinates (x, y) in the other radiation image is $G2(x, y)$, a pixel value at coordinates (x, y) in the bone part image is $Gb(x, y)$, a pixel value at coordinates (x, y) in the soft part image is $Gt(x, y)$, the first parameter is $\alpha$, and a second parameter is $\beta$, the bone part image is generated by Expression (1), and the soft part image is generated by Expression (4).

$$Gb(x,y)=G1(x,y)-\alpha\times G2(x,y) \qquad (1)$$

$$Gt(x,y)=G1(x,y)-\beta\times G2(x,y) \qquad (4)$$

It is preferable that the second emphasis processing is processing of subtracting the first emphasis image from any radiation image of the two radiation images.

It is preferable that the subject includes a bone part and a soft part, the first emphasis image is a bone part image, and the second emphasis image is a soft part image, and in a case in which a pixel value at coordinates (x, y) in one radiation image of the two radiation images is G1(x, y), a pixel value at coordinates (x, y) in the other radiation image is G2(x, y), a pixel value at coordinates (x, y) in the bone part image is Gb(x, y), a pixel value at coordinates (x, y) in the soft part image is Gt(x, y), and the first parameter is α, the bone part image is generated by Expression (1), and the soft part image is generated by Expression (2) or (3).

$$Gb(x,y)=G1(x,y)-\alpha\times G2(x,y) \qquad (1)$$

$$Gt(x,y)=G1(x,y)-Gb(x,y) \qquad (2)$$

$$Gt(x,y)=G2(x,y)-Gb(x,y) \qquad (3)$$

It is preferable that the correlation information is a correlation coefficient between a pixel value of the first emphasis image and a pixel value of the second emphasis image.

It is preferable that the image quality indicator is the correlation coefficient.

It is preferable that the processor performs control of setting a specific range in the image quality indicator as a reference range, and displaying, on the display unit, the image quality indicator and the reference range.

It is preferable that the processor performs control of giving a notification to a user in a case in which the image quality indicator is not included in the reference range.

Another aspect of the present invention relates to an operation method of a radiation image processing apparatus, the method comprising a step of acquiring two radiation images in which a specific subject is imaged by respectively using two types of radiation energies different from each other, a step of generating a first emphasis image by performing first emphasis processing on the two radiation images using an arithmetic expression including a first parameter, a step of generating a second emphasis image by performing second emphasis processing using at least any radiation image of the two radiation images, a step of generating correlation information indicating a correlation between the first emphasis image and the second emphasis image, and a step of performing control of displaying, on a display unit, the first emphasis image, a level value corresponding to a value of the first parameter, and an image quality indicator indicating a degree of difference between the first emphasis image and the second emphasis image, which is quantified based on the correlation information.

Still another aspect of the present invention relates to a non-transitory computer readable medium for storing a computer-executable program for causing a computer to execute a function of acquiring two radiation images in which a specific subject is imaged by respectively using two types of radiation energies different from each other, a function of generating a first emphasis image by performing first emphasis processing on the two radiation images using an arithmetic expression including a first parameter, a function of generating a second emphasis image by performing second emphasis processing using at least any radiation image of the two radiation images, a function of generating correlation information indicating a correlation between the first emphasis image and the second emphasis image, and a function of performing control of displaying, on a display unit, the first emphasis image, a level value corresponding to a value of the first parameter, and an image quality indicator indicating a degree of difference between the first emphasis image and the second emphasis image, which is quantified based on the correlation information.

According to the present invention, it is possible to easily and quickly generate the subtraction processing image in which the image quality is quantified and then adjusted.

DESCRIPTION OF THE PREFERRED EMBODIMENTS

An example of a basic configuration of the present invention will be described. A radiation image processing apparatus according to the embodiment of the present invention is a computer, such as a personal computer or a workstation, in which an application program for realizing a predetermined function is installed. A computer comprises a central processing unit (CPU) which is a processor, a memory, a storage, and the like, and various functions are realized by a program or the like stored in the storage.

Figure 1:
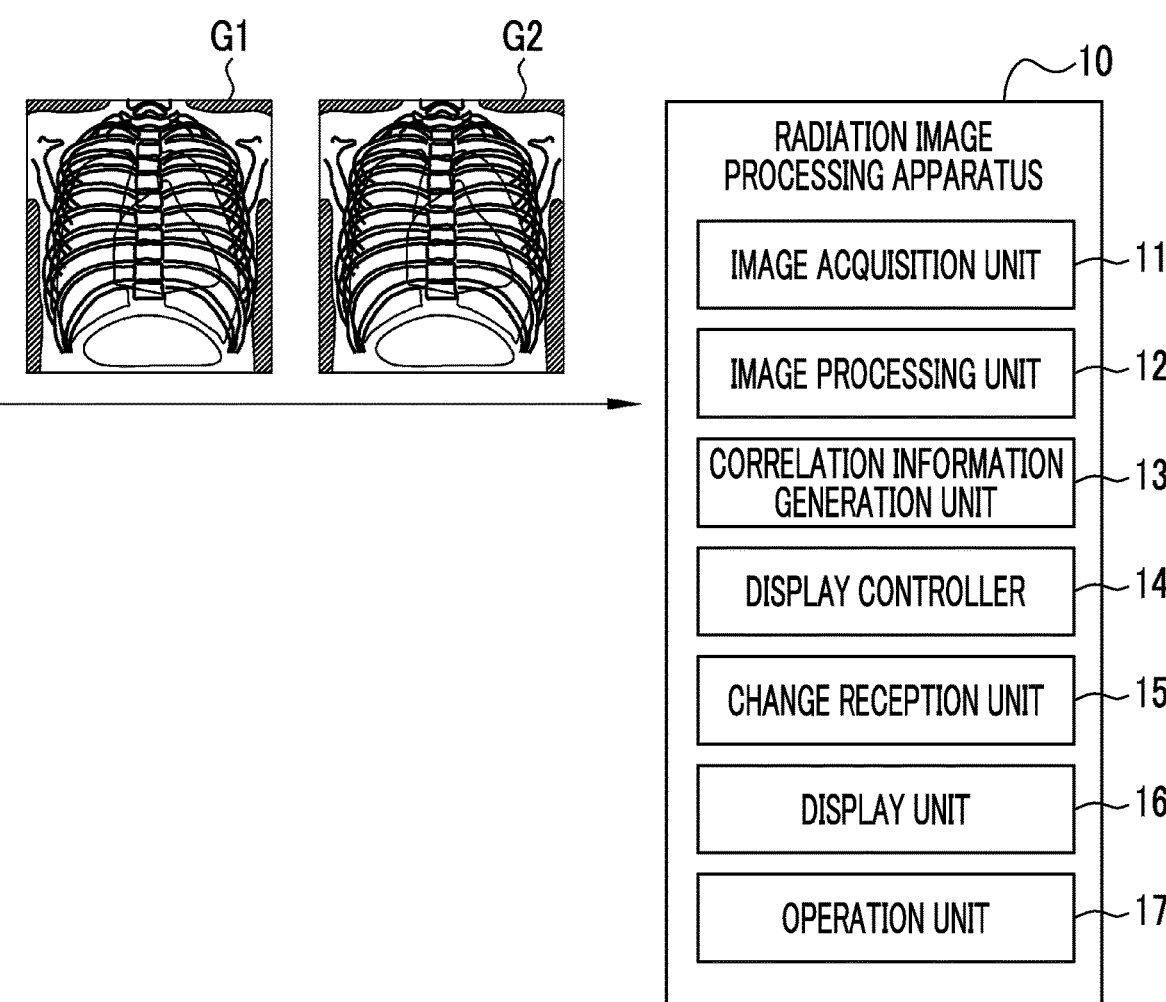
FIG. 1 is an explanatory diagram describing a function of a radiation image processing apparatus.

As shown in FIG. 1, a radiation image processing apparatus (hereinafter, referred to as processing apparatus) 10 according to the embodiment of the present invention comprises an image acquisition unit 11, an image processing unit 12, a correlation information generation unit 13, a display controller 14, a change reception unit 15, a display unit 16, and an operation unit 17.

The display unit 16 and the operation unit 17 need only be a device connected to a computer configuring the processing apparatus 10. The connection is not limited to direct connection, and may be connection via various networks. Therefore, in the processing apparatus 10, the display unit 16 or the operation unit 17 may be positioned at a position distant from the computer configuring the processing apparatus 10.

The image acquisition unit 11 acquires two radiation images in which a specific subject is imaged by respectively using two types of radiation energies different from each other. The specific subject means a subject, which is the same subject, in a case in which an imaging portion and an imaging direction are common in the two captured radiation images. The imaging using two types of radiation energies different from each other means that, in a case in which the radiation image is formed or the radiation is detected at least twice, radiation qualities of the radiation (energy distribution (hereinafter, simply referred to as energy)) are substantially different from each other, and includes a case in which two types of radiation having different radiation qualities are respectively used through a radiation energy conversion filter or the like, in addition to a case in which the radiation qualities of the radiation emitted by radiation sources are different from each other. Therefore, the two radiation images are different from each other.

The image acquisition unit 11 may acquire a plurality of three or more radiation images in a case of acquiring two radiation images. For example, the two radiation images different from each other may be acquired by acquiring two radiation images among a plurality of (three or more) radiation images different from each other in which the specific subject is imaged by respectively using a plurality of (three types or more) radiation energies different from each other.

In a case of acquiring the two radiation images, the image acquisition unit 11 may acquire a radiation image subjected to various types of processing, such as scattered ray correction processing or other image processing, in addition to a so-called original image (image that is not subjected to the image processing or the like). In addition, the image acquisition unit 11 may be configured to obtain, as at least one of the two acquired radiation images, the radiation image subjected to the scattered ray correction processing or the like. The scattered ray correction processing is image processing of performing correction of reducing scattered rays of the radiation due to the subject or the like. The scattered ray correction processing may be processing of removing a scattered ray component estimated according to a thickness of the subject for each pixel. The scattered ray correction processing may be performed by the image processing unit 12. The scattered ray correction processing will be described below.

The image processing unit 12 generates a first emphasis image by performing first emphasis processing on the two radiation images acquired by the image acquisition unit 11 by an arithmetic expression including a first parameter. In addition, the image processing unit 12 generates a second emphasis image by performing second emphasis processing using at least any radiation image of the two radiation images acquired by the image acquisition unit 11. The emphasis processing is processing of emphasizing a structure, an edge, or the like included in the radiation image by the image processing. The emphasis processing includes subtracting processing of removing a specific structure, noise, and the like from the radiation image. It should be noted that the radiation image also includes the radiation image after the image processing.

In the present embodiment, the first emphasis processing is processing of performing a first radiation image G1 and a second radiation image G2, which are the two radiation images, by the arithmetic expression including the first parameter. It should be noted that the change reception unit 15, which will be described below, receives a change of a level value corresponding to a value of the first parameter. The change reception unit 15 receives the change of the level value, so that the value of the first parameter is updated. The processing apparatus 10 repeatedly performs the series of pieces of processing by the processing apparatus 10 each time the value of the first parameter is updated.

It is preferable that the first emphasis processing is subtraction processing (hereinafter, referred to as energy subtraction (ES) processing). In the present embodiment, the first radiation image G1 and the second radiation image G2, which are the two radiation images, are subjected to the ES processing using the arithmetic expression including the first parameter. Specifically, the first emphasis image, which is the bone part image Gb, is generated by performing the ES processing based on the first radiation image G1 and the second radiation image G2, which is acquired by the image acquisition unit 11, in which a chest of a person is imaged as the specific subject. It should be noted that the image generated by the ES processing is referred to as an ES image. The bone part image Gb is the ES image.

In the subtraction processing, by a weighting operation in which one image of the two radiation images is weighted and subtracted from the other image, a signal caused by a specific tissue, such as a bone part or a soft part, in the processing image of arithmetic processing or the like can be reduced according to a parameter, which is a weighting coefficient. In the present embodiment, the subtraction processing can be executed as processing using the arithmetic expression including a first parameter $\alpha$ or a second parameter $\beta$ using the two radiation images of the radiation image G1 and the radiation image G2.

In a case in which weighting subtraction using the first parameter is performed between the respective corresponding pixels on the two radiation images of the radiation image G1 and the radiation image G2, for example, as shown in Expression (1), a pixel value $Gb(x, y)$ of coordinates $(x, y)$ at a specific position of the bone part image Gb is obtained in a manner that a corresponding pixel value $G2(x, y)$ of the radiation image G2 is weighted by the first parameter $\alpha$, which is the weighting coefficient, and then subtracted from the corresponding pixel value $G1(x, y)$ of the radiation image G1. In this case, it is preferable that the value of the first parameter $\alpha$ is set such that a pixel value indicating the soft part is substantially 0 in the bone part image Gb. It should be noted that the radiation image G1 and the radiation image G2 are images in which the specific subject is imaged, and the coordinates (x, y) of the radiation image G1 and the radiation image G2, which are the corresponding pixels, correspond to substantially the same positions of the subject. Also, the "corresponding pixels" mean pixels at a position corresponding to substantially the same position of the subject in a plurality of images.

$$Gb(x,y)=G1(x,y)-\alpha \times G2(x,y) \tag{1}$$

It should be noted that, in a case of selecting which radiation image, from which subtraction is performed, from among the two radiation images, either radiation image can be selected, but in the bone part image Gb, it is preferable that the subtraction is performed from the radiation image having a low radiation energy used for the imaging. The reason is that, in general, a radiation image having a lower radiation energy can obtain an image having a higher contrast of the bone part than a radiation image having a higher radiation energy. In the present embodiment, the radiation image G1 has a lower energy used for generating the radiation image than the radiation image G2.

It should be noted that, first, a predetermined value is set in advance for the first parameter α. Therefore, the predetermined value is set in advance for the first parameter α, and first, processing is performed on the first radiation image G1 and the second radiation image G2 by the arithmetic expression using the first parameter α of the predetermined value. As a result, the bone part image Gb is generated as the first emphasis image.

The second emphasis processing is processing using at least any radiation image of the two radiation images. Therefore, the second emphasis processing includes two types, the subtracting processing using the radiation image G1 or the radiation image G2 and the first emphasis image, and the subtraction processing using the radiation image G1 and the radiation image G2.

In a case in which the second emphasis processing is the subtracting processing, the subtracting processing is processing of removing the first emphasis image from one of the two radiation images. Removing the image means that the pixel value is subtracted in the corresponding pixel. The second emphasis image is generated based on the pixel value as a result of performing the subtraction. In the present embodiment, the first emphasis image is the bone part image Gb. Therefore, in the second emphasis processing, the soft part image Gt is generated as the second emphasis image by removing the bone part image Gb from one of the two radiation images of the radiation image G1 and the radiation image G2.

Specifically, in the subtracting processing, as shown in Expression (2) or (3), a pixel value Gt(x, y) at a specific position of the soft part image Gt, which is the second emphasis image, is obtained by subtracting the bone part image Gb(x, y), which is the first emphasis image, from the corresponding pixel value G1(x, y) of the radiation image G1 or the corresponding pixel value G2(x, y) of the radiation image G2.

$$Gt(x,y)=G1(x,y)-Gb(x,y) \tag{2}$$

$$Gt(x,y)=G2(x,y)-Gb(x,y) \tag{3}$$

Figure 2:
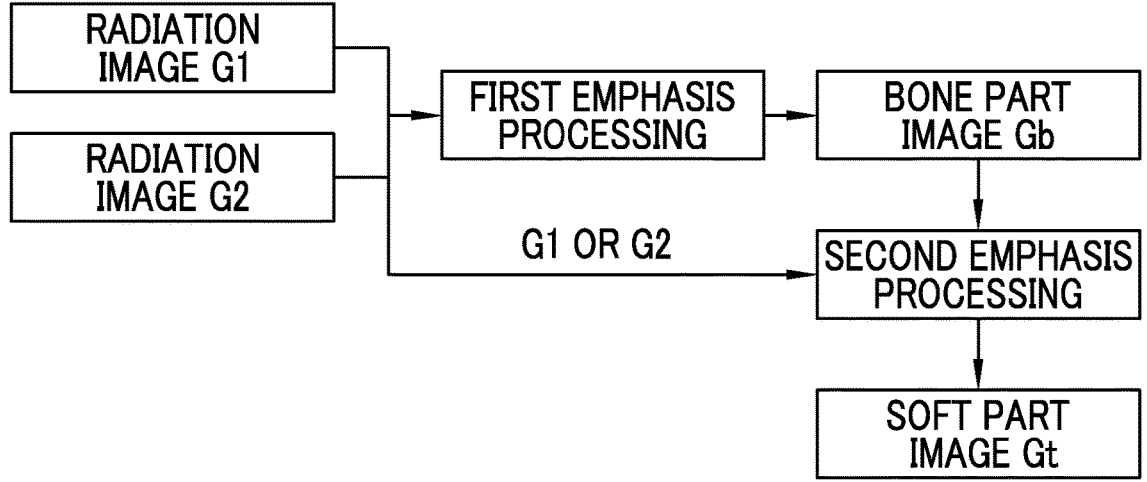
FIG. 2 is an explanatory diagram describing an example of generation of a bone part image Gb and generation of a soft part image Gt by using a bone part image Gb.

Therefore, a method of deriving the bone part image Gb and the soft part image Gt in a case in which the second emphasis processing is the subtracting processing is a method of, as shown in FIG. 2, deriving the soft part image Gt by deriving the bone part image Gb and removing the derived bone part image Gb from the original radiation image G1 or radiation image G2. Expression (1) is used in a case of deriving the bone part image Gb, and Expression (2) or Expression (3) is used in a case of deriving the soft part image Gt.

$$Gb(x,y)=G1(x,y)-\alpha \times G2(x,y) \tag{1}$$

$$Gt(x,y)=G1(x,y)-Gb(x,y) \tag{2}$$

$$Gt(x,y)=G2(x,y)-Gb(x,y) \tag{3}$$

In a case in which the second emphasis processing is the subtraction processing, the second emphasis processing is processing using the arithmetic expression including the second parameter for the two radiation images. The second emphasis processing in this case is the same processing as the first emphasis processing except that the parameters are different. Therefore, it is preferable that the second emphasis processing in this case is the same ES processing as the first emphasis processing, and it is preferable that the second emphasis processing is processing in which one radiation image of the two radiation images is weighted using the second parameter and then subtracted from the other radiation image.

For example, as shown in Expression (4), the pixel value Gt(x, y) at the specific position of the soft part image Gt, which is the second emphasis image, is obtained in a manner that a corresponding pixel value G1(x, y) of the radiation image G1 is weighted by the second parameter β and then subtracted from the corresponding pixel value G2(x, y) of the radiation image G2. In this case, it is preferable that the second parameter β is set such that a pixel value indicating the bone part is substantially 0 in the soft part image Gt. It should be noted that, in a case in which the first parameter α and the second parameter β are not distinguished from each other, the first parameter α and the second parameter β are referred to as an ES coefficient.

$$Gt(x,y)=G1(x,y)-\beta \times G2(x,y) \tag{4}$$

Figure 3:
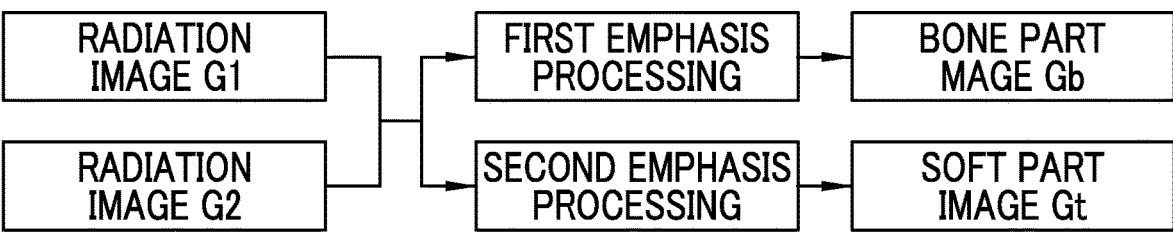
FIG. 3 is an explanatory diagram describing an example in which the bone part image Gb and the soft part image Gt are independently generated.

Therefore, a method of deriving the bone part image Gb and the soft part image Gt in a case in which the second emphasis processing is the subtraction processing is a processing of, as shown in FIG. 3, independently deriving the bone part image Gb by the first emphasis processing and the soft part image Gt by the second emphasis processing, by using the radiation image G1 and the radiation image G2 in each of the first emphasis processing and the second emphasis processing. Expression (1) using the first parameter α is used in a case of deriving the bone part image Gb in the first emphasis processing, and Expression (4) using the second parameter β is used in a case of deriving the soft part image Gt in the second emphasis processing.

$$Gb(x,y)=G1(x,y)-\alpha \times G2(x,y) \tag{1}$$

$$Gt(x,y)=G1(x,y)-\beta \times G2(x,y) \tag{4}$$

It should be noted that, in the embodiment described above, the bone part image Gb is derived by the first emphasis processing, but the soft part image Gt may be derived by the first emphasis processing, and the bone part image Gb may be derived by the second emphasis processing. Therefore, the soft part image Gt may be derived as the first emphasis image in the first emphasis processing, and the bone part image Gb may be derived as the second emphasis image by removing the soft part image Gt from one of the two radiation images of the radiation image G1 and the radiation image G2 in the second emphasis processing.

The method of deriving the soft part image Gt by the first emphasis processing is the same as a case in which the bone part image Gb is derived by the first emphasis processing.

That is, weighting subtraction using the second parameter is performed between the respective corresponding pixels on the two radiation images of the radiation image G1 and the radiation image G2. This case is the same as a case in which the soft part image Gt is derived using Expression (4).

$$Gt(x,y)=G1(x,y)-\beta\times G2(x,y) \tag{4}$$

Then, in the subtracting processing, which is the second emphasis processing, as shown in Expression (5) or (6), a pixel value Gb(x, y) at a specific position of the bone part image Gb, which is the second emphasis image, is obtained by subtracting the soft part image Gt(x, y), which is the first emphasis image, from the corresponding pixel value G1(x, y) of the radiation image G1 or the corresponding pixel value G2(x, y) of the radiation image G2.

$$Gb(x,y)=G1(x,y)-Gt(x,y) \tag{5}$$

$$Gb(x,y)=G2(x,y)-Gt(x,y) \tag{6}$$

Figure 4:
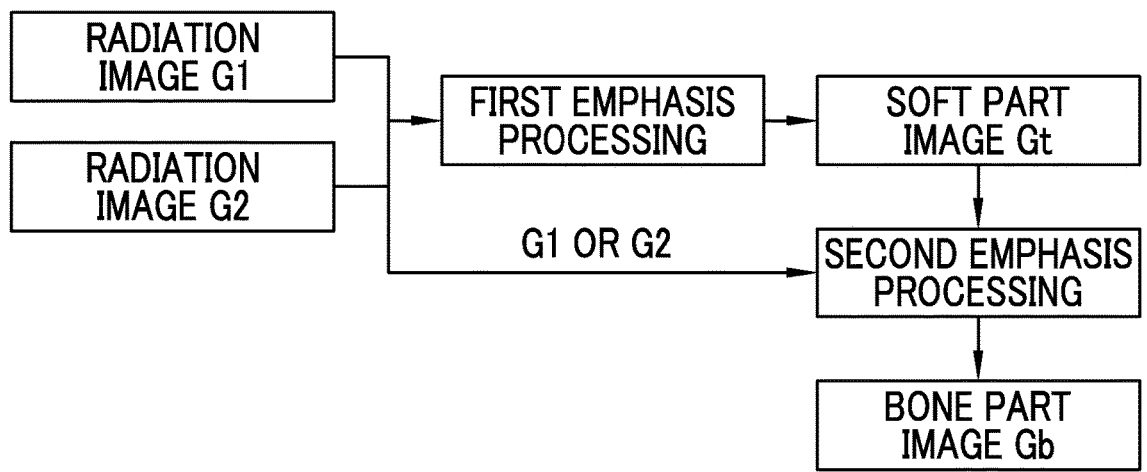
FIG. 4 is an explanatory diagram describing an example of generation of the soft part image Gt and generation of the bone part image Gb by using the soft part image Gt.

Therefore, a method of deriving the bone part image Gb and the soft part image Gt in a case in which the second emphasis processing is the subtracting processing may be a method of, as shown in FIG. 4, deriving the bone part image Gb by deriving the soft part image Gt and removing the derived soft part image Gt from the original radiation image G1 or radiation image G2. Expression (4) is used in a case of deriving the soft part image Gt, and Expression (5) or Expression (6) is used in a case of deriving the bone part image Gb.

$$Gt(x,y)=G1(x,y)-\beta\times G2(x,y) \tag{4}$$

$$Gb(x,y)=G1(x,y)-Gt(x,y) \tag{5}$$

$$Gb(x,y)=G2(x,y)-Gt(x,y) \tag{6}$$

It should be noted that, in the subtracting processing, in a case of selecting which radiation image, from which subtraction is performed, from among the two radiation images, either radiation image can be selected, but a case in which the radiation image having a high radiation energy used for the imaging is selected is preferable because an image in which the bone part is removed in a better manner is obtained. The reason is that, in general, a radiation image having a higher radiation energy can obtain an image having a lower contrast of the bone part than a radiation image having a lower radiation energy.

It should be noted that, first, a predetermined value is set in advance for the second parameter 3. Therefore, the predetermined value is set in advance for the second parameter β, and first, processing is performed on the first radiation image G1 and the second radiation image G2 by the arithmetic expression using the second parameter β of the predetermined value. As a result, the soft part image Gt is generated as the second emphasis image. The soft part image Gt is the ES image.

It should be noted that, in a case in which the acquired radiation image is not subjected to contrast correction processing, it is preferable that the image processing unit 12 performs, on the acquired radiation image, the contrast correction processing of correcting a difference in contrast according to the tube voltage during the imaging of the two radiation images and a decrease in the contrast due to an influence of beam hardening. A known method can be adopted for the contrast correction processing.

Figure 5:
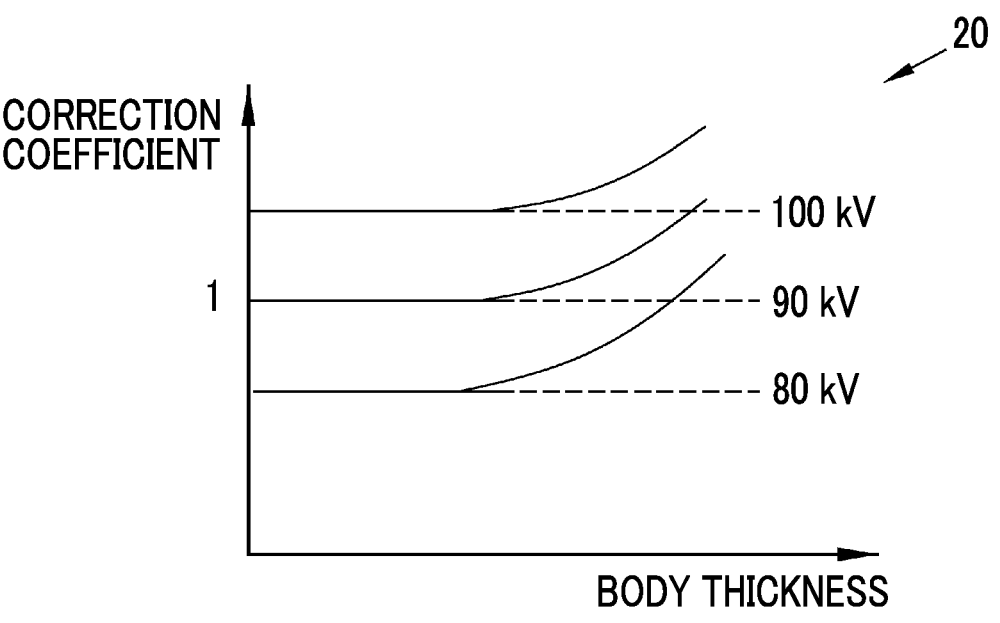
FIG. 5 is a look-up table showing a correction coefficient depending on a body thickness and a tube voltage, and is a case in which the tube voltages are 100 kV, 90 kV, and 80 kV, respectively.

FIG. 5 shows a look-up table for acquiring a correction coefficient for correcting a difference in contrast of the bone part image Gb according to the tube voltage during the imaging and a decrease in contrast due to the influence of beam hardening. The correction coefficient is a coefficient for correcting each pixel value Gb(x, y) of the bone part image Gb. A look-up table LUT 20 is shown in which a reference imaging condition is set to the tube voltage of 90 kV.

As shown in FIG. 5, in the look-up table LUT 20, the correction coefficient is set to be larger as the tube voltage is higher and a body thickness of the subject is larger. It should be noted that although the look-up table LUT 20 is shown in two dimensions in FIG. 5, the correction coefficient differs depending on the pixel value of the bone region. Therefore, the look-up table LUT 20 is actually a three-dimensional table to which an axis representing the pixel value of the bone region is added.

For the soft part image Gt, similarly to the bone part image Gb, as the contrast correction processing, it is possible to correct the fluctuation of the pixel value Gt(x, y) of the soft part image Gt by using a look-up table (not shown) for obtaining the correction coefficient according to the soft part image Gt.

The correlation information generation unit 13 generates correlation information indicating a correlation between the first emphasis image and the second emphasis image. In a case in which the correlation is low, the first emphasis image and the second emphasis image are images having a high degree to which the images are different from each other, and in a case in which the correlation is high, the first emphasis image and the second emphasis image are images having a high degree to which the images are the same, and thus it is possible to quantify the degree of difference between the first emphasis image and the second emphasis image according to the image quality indicator based on the correlation information. Therefore, as for the correlation information, it is preferable to convert to the image quality indicator such that the image quality as the ES image is higher as the correlation between the first emphasis image and the second emphasis image is lower, and the image quality as the ES image is lower as the correlation between the first emphasis image and the second emphasis image is higher.

Examples of the correlation information include a correlation value. Specifically, a correlation value calculated by any calculation method can be used as long as the correlation value indicates a degree of correlation between the images, such as a statistically calculated correlation coefficient or a correlation value in sum of absolute difference (SAD), sum of squared difference (SSD), normalized cross-correlation (NCC), or zero-mean normalized cross-correlation (ZNCC) used in template matching technique.

By generating the correlation information related to the first emphasis image and the second emphasis image as the correlation value, the degree of difference between the first emphasis image and the second emphasis image is quantified. Therefore, in a case in which it is preferable that the first emphasis image and the second emphasis image are different from each other, it is most preferable that the correlation value is a correlation value indicating a maximum degree of difference in the quantified degree of difference.

In the present embodiment, the correlation coefficient used in statistics calculated by using the pixel value of the first emphasis image and the pixel value of the second emphasis image is used as the correlation information which is the correlation value indicating the degree of the correlation. The correlation coefficient may be calculated for the entire first emphasis image and second emphasis image, or may be calculated for a region of interest of the first emphasis image and a corresponding region of interest of the second emphasis image.

A specific calculation method of a correlation coefficient r between a pixel value of the region of interest of the first emphasis image and a pixel value of the corresponding region of interest of the second emphasis image is as follows. The correlation coefficient r between a first pixel value in the region of interest of the bone part image Gb, which is the first emphasis image, and a second pixel value of the corresponding region of interest in the soft part image Gt, which is the second emphasis image, is calculated from a standard deviation sa of the first pixel value, a standard deviation sb of the second pixel value, and a covariance sab between the first pixel value and the second pixel value by Expression (7).

$$r = \frac{sab}{sa \cdot sb} \tag{7}$$

The standard deviation sa of the first pixel value, the standard deviation sb of the second pixel value, and the covariance sab between the first pixel value and the second pixel value are calculated by Expressions (8), (9), and (10), respectively. It should be noted that the pixel value of each coordinate in the region of interest of the bone part image Gb is a first pixel value ai (i is an integer), and the numerical value of the pixel value of each coordinate in the region of interest of the soft part image Gt, which is the second emphasis image, is a second pixel value bi (i is an integer). Then, an average value of the first pixel values ai is an average value A, an average value of the second pixel values bi is an average value B, and the total number of the first pixel value ai and the second pixel value bi is a total number n.

$$sa = \sqrt{\frac{1}{n}\sum_{1}^{n}(ai - A)^2} \tag{8}$$

$$sb = \sqrt{\frac{1}{n}\sum_{1}^{n}(bi - B)^2} \tag{9}$$

$$sab = \frac{1}{n}\sum_{1}^{n}(ai - A)(bi - B) \tag{10}$$

Therefore, the correlation coefficient r between the first pixel value ai and the second pixel value bi can be calculated by Expression (11).

$$r = \frac{\frac{1}{n}\sum_{1}^{n}(ai - A)(bi - B)}{\sqrt{\frac{1}{n}\sum_{1}^{n}(ai - A)^2} \cdot \sqrt{\frac{1}{n}\sum_{1}^{n}(bi - B)^2}} \tag{11}$$

The correlation coefficient r has a value in a range of 1 to −1, and a positive correlation between the first pixel value ai and the second pixel value bi is stronger as the correlation coefficient r is closer to 1, a negative correlation is stronger as the correlation coefficient r is closer to −1, and the correlation is less as the correlation coefficient r is closer to 0. Since the bone part image Gb and the soft part image Gt are generated by subtracting the image signal of the soft part or the bone part from each of the two radiation images, the first pixel value ai of the bone part image Gb and the second pixel value bi of the soft part image Gt have a lower degree to which the same pixel value is commonly included at a specific position and a higher degree to which the images are different from each other as the correlation coefficient r is closer to 0. Therefore, in a case in which the bone part image Gb and the soft part image Gt have a high degree to which the images are different from each other, it can be said that the image quality as the bone part image Gb is high, and the image quality as the soft part image Gt is high. It should be noted that, in the present specification, the "image quality" of the ES image is related to the presence or absence of the image or the pixel value based on the ES image other than a target structure, tissue, or the like. As described above, the correlation coefficient r between the first pixel value ai of the bone part image Gb and the second pixel value bi of the soft part image Gt is appropriate as the image quality indicator of the bone part image Gb and the soft part image Gt, and it can be said that the image quality of the bone part image Gb or the soft part image Gt is higher as the correlation coefficient r is closer to 0, that is, the image quality indicator is closer to 0.

It should be noted that the correlation coefficient r between the first pixel value ai of the bone part image Gb and the second pixel value bi of the soft part image Gt is changed as the bone part image Gb and/or the soft part image Gt is changed. A case in which the bone part image Gb is changed is a case in which the first parameter α is updated from a previous value. A case in which the soft part image Gt is changed includes two cases depending on the content of the second emphasis processing in a case of generating the soft part image Gt, which are a case in which the bone part image Gb is changed and a case in which the second parameter β is updated from a previous value. It is preferable that the correlation information generation unit 13 generates the correlation information each time the ES image is generated. Therefore, in the present embodiment, it is preferable that the correlation information generation unit 13 calculates the correlation coefficient r each time the bone part image Gb and/or the soft part image Gt is changed.

The display controller 14 performs control of displaying, on the display unit 16, the first emphasis image, the level value corresponding to the value of the first parameter used in a case of generating the first emphasis image, and the image quality indicator indicating the degree of difference between the first emphasis image and the second emphasis image, which is quantified based on the correlation information. A user of the processing apparatus 10 can check the first emphasis image displayed on the display unit 16, the level value, and the image quality indicator on the screen of the display unit 16.

The display unit 16 is, for example, a liquid crystal display, and displays the captured radiation image, the processing image generated by the radiation image processing apparatus 10, and the like. In the present embodiment, the display unit 16 is the display. The operation unit 17 is, for example, a keyboard and/or a pointing device for operating the processing apparatus 10. The display unit 16 and the operation unit 17 can be configured with a touch panel. In the present embodiment, the operation unit 17 gives various instructions, such as input, selection, or change via a graphical user interface (GUI) displayed on the display.

As an ES image quality indicator, which is the image quality indicator indicating the degree of difference between the first emphasis image and the second emphasis image, which is quantified based on the correlation information, an ES image quality indicator being based on the correlation information and representing the image qualities of the first emphasis image and the second emphasis image which are quantified is used. It is preferable that the ES image quality indicator is the ES image quality indicator that allows easy understanding of the superiority or inferiority of the image quality of the first emphasis image or the second emphasis image depending on a high or low value of the image quality indicator. The ES image quality indicator may be a value obtained by converting the correlation value of the correlation information or the like according to the type of the correlation information, or may be the correlation value of the correlation information itself.

In the present embodiment, the ES image quality indicator is set to the correlation coefficient r itself. By setting the ES image quality indicator to the correlation coefficient r itself, the correlation value has a value within a range of −1 or more and +1 or less, so that it is easy to understand the superiority or inferiority of the image quality of the ES image. According to such an ES image quality indicator, an image quality (hereinafter, referred to as ES image quality) based on the correlation information of the ES image is better as an absolute value of the ES image quality indicator is lower and closer to 0, it cannot be said that the ES image quality of the ES image is better as the absolute value of the ES image quality indicator is higher and closer to −1 or +1, and it is shown that there is a possibility that there is room for adjustment of the image quality for the ES image quality.

Figure 6:
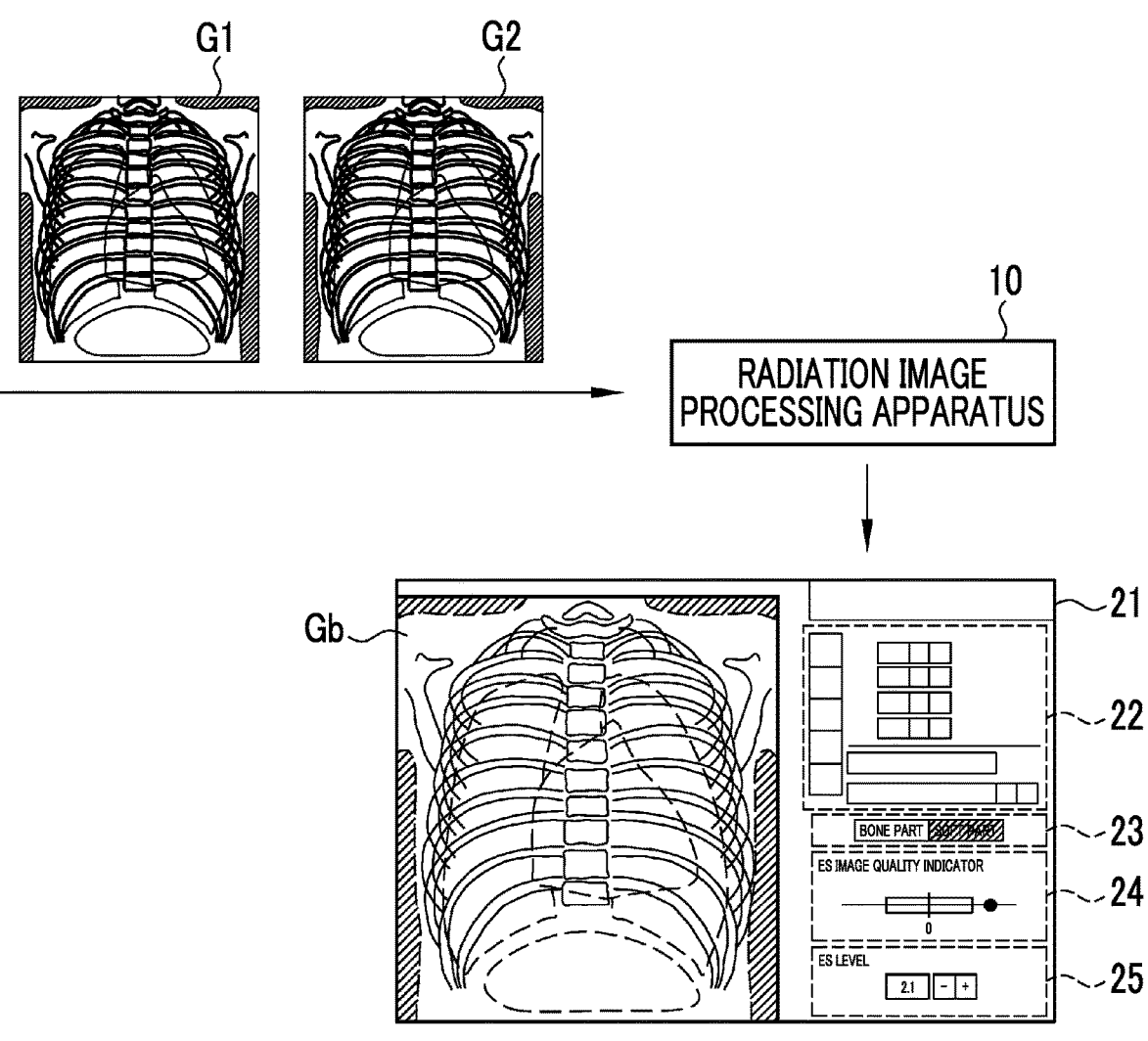
FIG. 6 is an explanatory diagram describing display of a screen 21 by the radiation image processing apparatus.

As shown in FIG. 6, in the present embodiment, the bone part image Gb, which is the first emphasis image, is displayed on a screen 21 of the display. The screen 21 includes, in addition to the bone part image Gb, an image adjustment unit 22 that performs various general adjustments in a case of generating the bone part image Gb, an ES image switching unit 23 that gives an instruction to switch the type of the ES image or the radiation image to be displayed on the screen 21, an ES image quality indicator display unit 24 that displays the ES image quality indicator of the displayed bone part image Gb, and an ES level display unit 25 that displays the level value corresponding to the value of the first parameter α used in a case of generating the displayed bone part image Gb.

Figure 7:
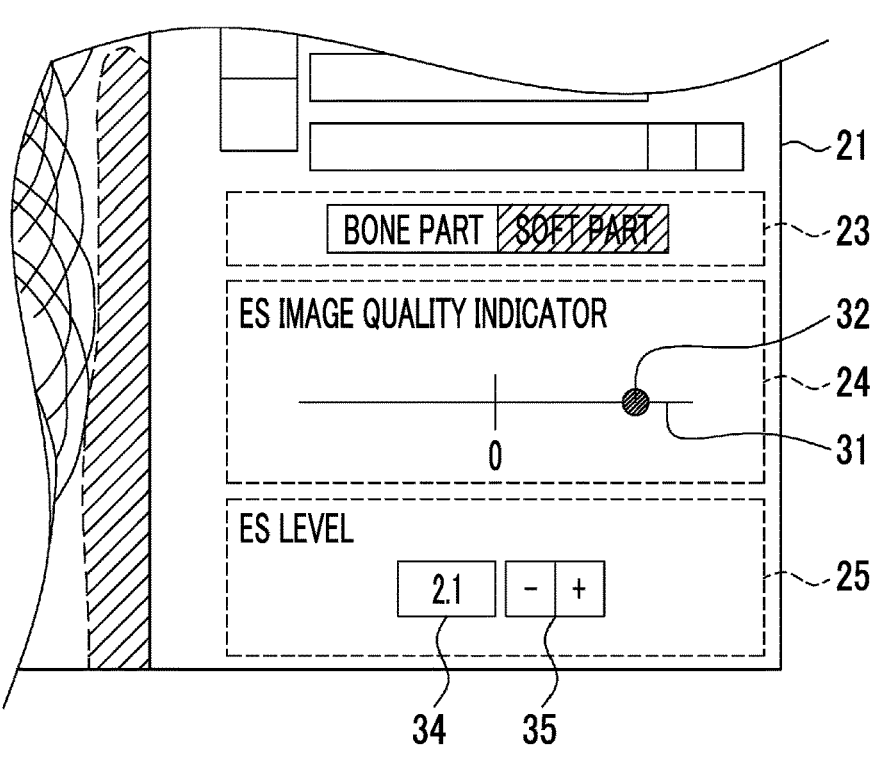
FIG. 7 is an explanatory diagram describing display of an image quality indicator and an ES level value of an ES image before the ES level value is changed.

The ES image switching unit 23 gives the instruction to switch the type of the ES image to be displayed on the screen 21. The ES image switching unit 23 may be configured to switch and display the radiation image in addition to switching the ES image. As shown in FIG. 7, in a case in which the type of the ES image includes the bone part image Gb and the soft part image Gt, any option of the "bone part" or the "soft part" displayed on the screen 21 by the GUI or the like is selected to select the type of the ES image to be displayed on the screen 21. In the ES image switching unit 23, it is preferable that which of the options of "bone part" and "soft part" is selected according to the selection of the type of the ES image is displayed in a form in which the options can be grasped at a glance by, for example, displaying the option, which is not selected, darkly and displaying the selected option brightly. The selected ES image type is displayed on a left portion of the screen 21 in a case of facing the screen 21. In the present embodiment, the bone part image Gb is selected by the ES image switching unit 23, and the bone part image Gb is displayed on the screen 21.

It is preferable that the ES image quality indicator display unit 24 shows the ES image quality indicator in a form in which the ES image quality indicator can be easily grasped. The display form of the ES image quality indicator is set according to the type of the ES image. The display form of the ES image quality indicator need only be a form in which the user can grasp the ES image quality indicator.

In the present embodiment, since the ES image quality indicator is the correlation coefficient r itself, the ES image quality indicator is displayed in a form of a number line 31 indicating −1 to 1 with a scale on 0 at the origin. The ES image quality indicator of the bone part image Gb displayed on the screen 21 is indicated by a point 32 on the number line 31. As a result, it is possible to grasp at a glance whether the ES image quality indicator of the bone part image Gb displayed on the screen 21 is relatively close to or far from the scale of 0, which is the most preferable ES image quality.

The adjustment of the ES image quality is performed by regenerating the ES image. As described above, the ES image is generated by performing the processing by the arithmetic expression including the ES coefficient on the two radiation images acquired by the image processing unit 12. Therefore, it is possible to generate the ES image of which the image quality is adjusted by changing the ES coefficient used in a case of generating the ES image and regenerating the ES image using the changed ES coefficient.

Regarding the change of the ES coefficient, the value of the ES coefficient used for generating the ES image may be used as it is, but it is preferable that the value converted into the ES level value, which is the level value corresponding to the ES coefficient, is used. For example, the ES level value is a preset numerical range corresponding to the ES coefficient. In this case, the numerical range can be, for example, a range of 0 or more and 10 or less or a range of 0 or more and 100 or less. As a result, the user can easily recognize a relationship between the change of the value of the ES coefficient and a degree of adjustment of the ES image quality.

The ES level display unit 25 includes an ES level value display unit 34 and an ES level value change unit 35. The ES level value display unit 34 displays the level value, which is the ES level value of the bone part image Gb displayed on the screen 21, as a numerical value. For example, the level value in a case of generating the bone part image Gb displayed on the screen 21 is displayed as "2.1". In the present embodiment, as the level value, a value in which a numerical value in a range of 1 or more and 10 or less, to which the value of the first parameter α is associated, is indicated by one digit of the decimal point is used. The ES level value change unit 35 is displayed by the GUI, and has a button for changing the ES level value. The button consists of, for example, a plus button displayed as "+" and a minus button displayed as "−".

The change reception unit 15 receives the change of the ES level value. In a case in which the change of the ES level value which is the level value is received, the change reception unit 15 updates the value of the first parameter corresponding to the ES level value. In a case in which the value of the first parameter is updated, the series of pieces of processing using the updated value of the first parameter are performed again, and the control of displaying, on the display unit 16, each of a new first emphasis image, a new level value, and a new image quality indicator is performed. Therefore, each time the change of the level value is received, the series of pieces of processing described above is performed again.

Specifically, in a case in which the change reception unit 15 receives the change of the ES level value, the image processing unit 12 performs the first emphasis processing using the updated value of the first parameter to generate and update the first emphasis image, and in some cases, performs the second emphasis processing using the updated first emphasis image. The correlation information generation unit 13 and the display controller 14 also perform the processing again using the updated first emphasis image, and the updated first emphasis image and the level value corresponding to the updated first parameter, and the updated image quality indicator are displayed on the display unit 16.

As described above, each time the change reception unit 15 receives the change of the ES level value, the processing from the generation of the processing image to the display of the image quality indicator described above is repeated. The user may change the ES level value again by viewing the image quality indicator displayed on the display and the regenerated first emphasis image, or may terminate the processing in a case in which it is considered that the ES image quality is improved.

It should be noted that, in order for the change reception unit 15 to receive the change of the ES level value, it is preferable that the display controller 14 performs control of displaying, on the display which is the display unit 16, a user interface that receives the change of the ES level value by the user. The user interface or the like need only be a user interface that can receive the change of the ES level value by the user, and the aspect thereof or the like is not limited.

Figure 8:
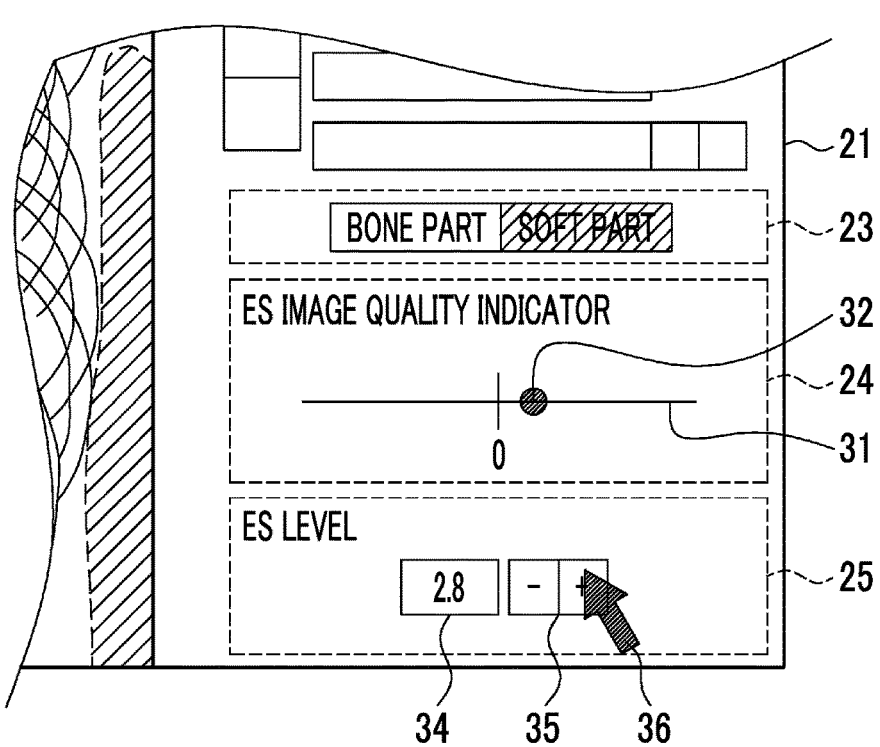
FIG. 8 is an explanatory diagram describing display of the image quality indicator and the ES level value of the ES image after the ES level value is changed.

As shown in FIG. 8, in the present embodiment, the user operates the ES level value change unit 35 with the operation unit 17, such as a mouse or a keyboard, to change the ES level value. For example, in a case in which the operation unit 17 is the mouse, an arrow-shaped cursor 36 is displayed on the screen 21, and the ES level value displayed on the ES level value display unit 34 can be increased or decreased by clicking a button selected by the cursor 36. In FIG. 8, the value is changed from "2.1" to "2.8". In a case in which the changed ES level value is displayed on the ES level value display unit 34, the change reception unit 15 receives the change of the ES level value, and the subsequent processing is automatically proceeded as described above. The bone part image Gb regenerated corresponding to the changed ES level value is displayed, and the image quality indicator of the regenerated bone part image Gb is displayed as the point 32 on the ES image quality indicator display unit 24.

Figure 9:
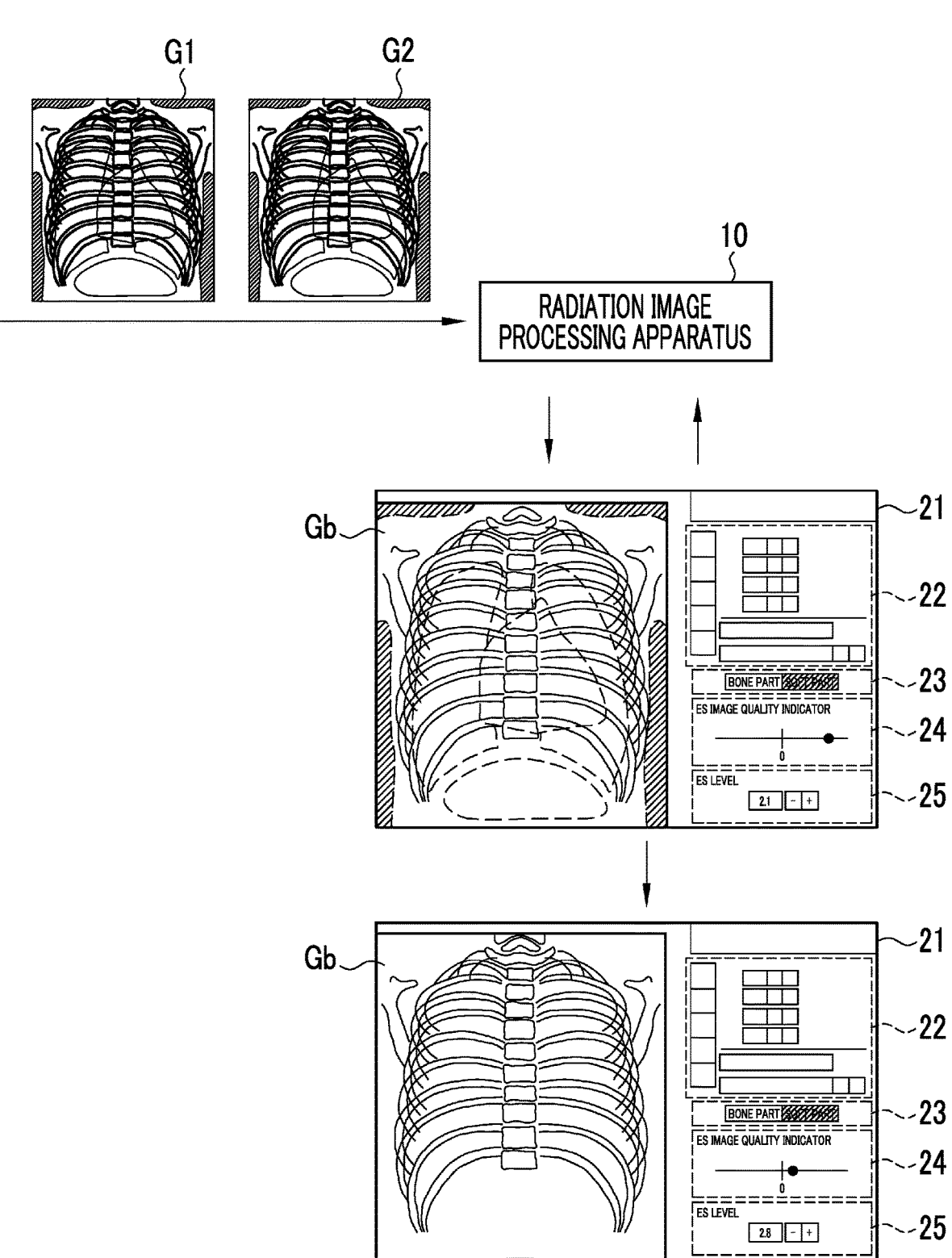
FIG. 9 is an explanatory diagram describing adjustment of an image quality of the ES image.

As shown in FIG. 9, in a case in which the image quality indicator of the regenerated first emphasis image is far from 0 which is the reference, the user can repeat the change of the ES level value a plurality of times to generate the first emphasis image with improved ES image quality. Each time the change reception unit 15 receives the change of the ES level value, the processing from the generation of the processing image to the display of the image quality indicator described above is repeated. Finally, in a case in which the point 32 indicating the ES image quality indicator of the changed bone part image Gb is closer to 0 which is the reference of the ES image quality indicator, the user can understand at a glance that the regenerated bone part image Gb is good as the ES image quality and is not required to be further adjusted, and the adjustment of the ES image quality is completed, by viewing the screen 21.

In this way, even in a case in which the change of the ES level value is repeated a plurality of times, since the changed ES image quality indicator is displayed each time, it is possible to know of how much the ES image quality indicator is to be improved or deteriorated by converting the ES level value. In this way, since the user can adjust the ES image by performing an operation at one place while checking the ES image on one screen 21, it is possible to easily and quickly perform the adjustment such that the ES image quality is closest to 0 which is the reference.

In the present embodiment, the description has been made in which the first emphasis image is the bone part image Gb, but the first emphasis image may be the soft part image Gt, and the second emphasis image may be the bone part image Gb.

In addition, in the present embodiment, the description has been made in which the radiation image is an X-ray image and the first emphasis image and the second emphasis image are the bone part image Gb and the soft part image Gt, but any radiation image can be adopted as long as the image in which the specific structure, tissue, or the like is extracted can be generated from the radiation image by the processing, such as the subtraction, on the two radiation images. For example, the radiation image may be a computed tomography (CT) image or the like, or the first emphasis image and the second emphasis image may be a blood vessel image and an image excluding blood vessels.

Figure 10:
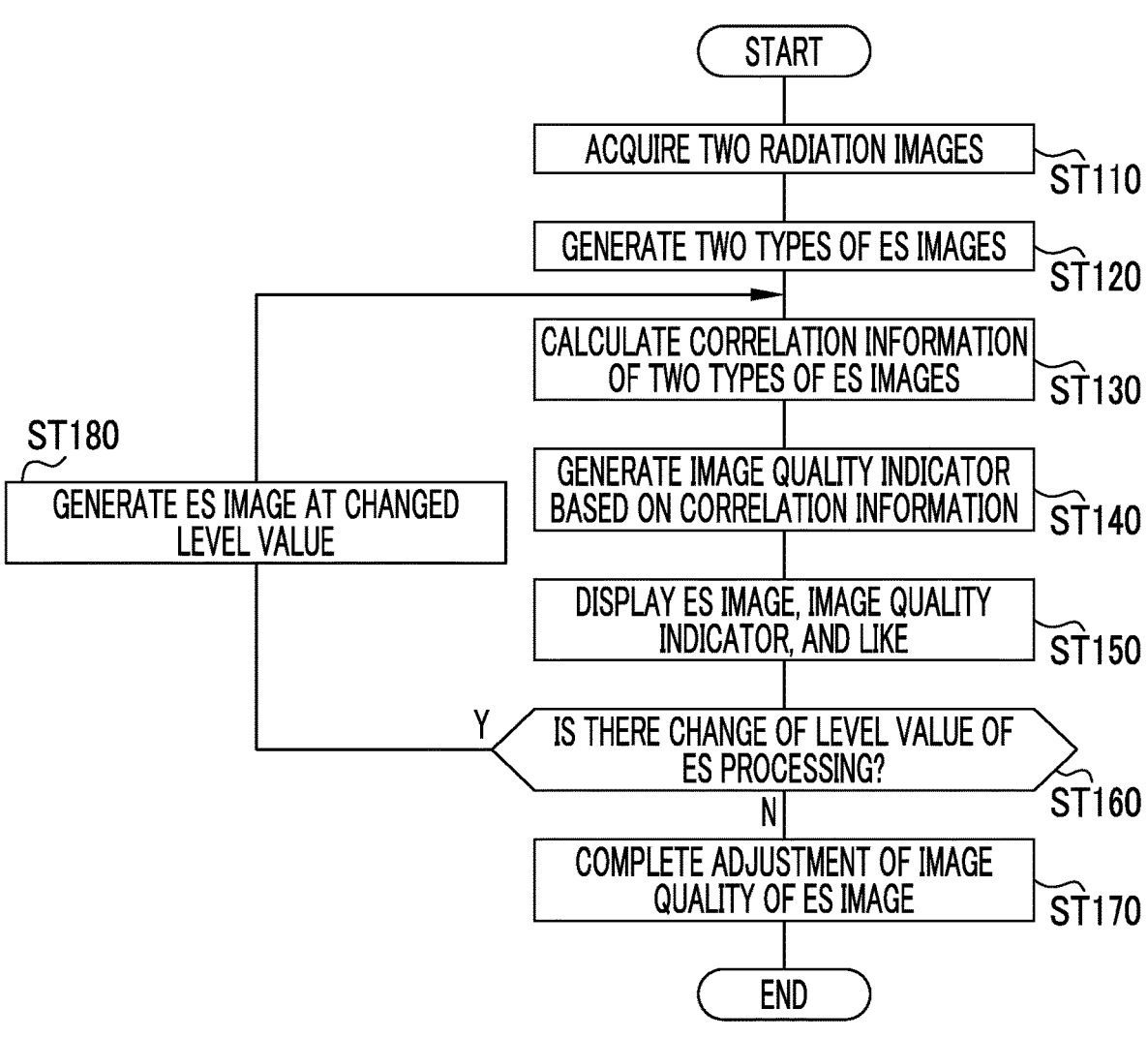
FIG. 10 is a flowchart describing a flow of processing of the radiation image processing apparatus.

Next, an example of a flow of the processing by the processing apparatus 10 according to the embodiment of the present invention will be described with reference to a flowchart shown in FIG. 10. The processing apparatus 10 acquires the first radiation image G1 and the second radiation image G2 in which the same region of the chest of the same subject is imaged as the specific subject in the same direction by respectively using two types of radiation energies different from each other (step ST110). The bone part image Gb is generated by performing the ES processing on the acquired first radiation image G1 and second radiation image G2 using the arithmetic expression including the first parameter. The soft part image Gt is generated by performing the processing of subtracting the bone part image Gb from the second radiation image G2, and two types of the ES images of the bone part image Gb and the soft part image Gt are generated (step ST120). Then, the correlation information between the bone part image Gb and the soft part image Gt is calculated (step ST130). The correlation information is the correlation coefficient r. Moreover, the value of the correlation coefficient r is used as the ES image quality indicator, and the image quality indicator is generated (step ST140).

Here, the image quality of the bone part image Gb out of the bone part image Gb and the soft part image Gt is adjusted. Therefore, the bone part image Gb, the ES image quality indicator, and the level value, which is the ES level value based on the first parameter α used in the arithmetic expression in a case of generating the bone part image Gb, are displayed on the display (step ST150). The radiologist who is the user decides whether or not to change the ES level value based on the displaying on the display. In a case in which the ES level value is changed (Y in step ST160), the bone part image Gb is regenerated by performing the ES processing using the arithmetic expression including the first parameter based on the changed ES level value (step ST180). In a case in which the ES level value is not changed (N in step ST160), the adjustment of the image quality of the bone part image Gb is completed (step ST170).

In the ES image, an error may occur due to a fluctuation of an output value of radiation, a variation of the subject, or the like, and the image quality may be deteriorated. For example, in the generated bone part image Gb, excessive disappearance the bone part or a remaining portion of the bone part may occur. Regarding the excessive disappearance and the remaining portion, two causes include, firstly, a temporal change of the radiation source and/or a radiography panel in a radiography apparatus (see FIG. 11). The radiation quality and/or the radiation dose of the radiation is changed with the temporal change due to deterioration of the tube in the radiation source. In addition, the pixel value to be output is changed with the temporal change due to deterioration of the radiography panel or the like.

In addition, in the correction coefficient using the LUT 20 (see FIG. 5) or the like for correcting the decrease in the contrast, in order to set tube voltage information, an error of the correction coefficient occurs in a case in which the actual radiation quality is changed. In addition, the body thickness is obtained from a difference between a pixel value I0 in a case in which the subject is not present and a pixel value I in a case in which the subject is present in the imaging. However, the pixel value I0 is calculated based on calibration data acquired in advance by using a set imaging condition information, such as the tube voltage (kV value), the radiation dose (mAs value), and a source image receptor distance (SID). Therefore, in a case in which the actual radiation quality and radiation dose of the radiation, or output value of the radiography panel, or the like is changed as compared with a case in which the calibration data is acquired, an error occurs in the calculated pixel value I0, and the body thickness or the correction coefficient in the LUT 20 is deviated. For these reasons, an error may occur in the ES image, such as the bone part image Gb to be generated.

In addition, in a case of estimating the primary rays or the scattered rays, the body thickness is repeatedly obtained to match the pixel value I. The body thickness is obtained from a difference between the pixel value I0 in a case in which the subject is not present and the pixel value I in a case in which the subject is present. Therefore, in a case in which the radiation quality and the radiation dose of the radiation, or the output value of the radiography panel, or the like is changed, an error occurs in the calculated pixel value I0, the body thickness is deviated, and an error is included in the primary ray or scattered rays to be obtained. Therefore, since the bone part image Gb is calculated by the method described above using the pixel value of the radiation image which is the primary ray data including the error, an error may occur in the bone part image Gb which is the ES image.

Secondly, there is a case in which the variation of a subject thickness occurs. For example, in the LUT 20 (see FIG. 5), the pixel value Gb(x, y) of the bone part image Gb is corrected depending on the subject thickness. However, the body thickness of this relational expression is the body thickness at a standard fat ratio, and Gb(x, y) is corrected depending on the subject thickness. However, the fat ratio may be changed from a standard value depending on the subject and the part. Then, the deviation occurs in the correction coefficient of Gb(x, y), and the excessive disappearance or remaining portion of the bone occurs, in the ES image. Therefore, for example, in a case in which the deviation also occurs in the correction coefficient of the pixel value Gb(x, y) of the bone part image Gb, and the excessive disappearance or remaining portion of the bone occurs in the bone part image Gb, which is the ES image.

In a case in which it is considered that the error of the ES image, the excessive disappearance or remaining portion of the target structure, or the like occurs in the ES image as described above, it is required for the radiologist to adjust the image of the ES image. The radiologist visually checks the ES image, and adjusts the image quality. In a case in which a large amount of radiography such as a medical examination is required, the radiologist should complete the imaging one after another in a short time. Therefore, there is a case in which only the image quality of the normal radiation image is checked and a time for checking the image quality of the ES image created based on the radiation image is insufficient, and there is a case that the image quality of the ES image cannot be guaranteed during the imaging.

A solution to such a problem can be considered, such as improving a processing procedure, a processing speed, or the like of a system or a device that adjusts the image quality, but it is conceivable that a load is applied on the radiologist in a case in which the radiologist adjusts the image quality by visual evaluation of the radiation image or the ES image even after the solution is solved, for example. In addition, in this case, there is a possibility that a variation in an individual difference of the radiologist or the like may occur in the adjustment of the image quality.

With the processing apparatus 10 or the like, the ES image quality indicator indicating the ES image quality is quantified and displayed on the display. Therefore, the radiologist need only check at least the image quality indicator, and can reduce the load for checking the image or adjusting the image quality of the ES image. In addition, since the quantified image quality and the reference thereof as needed are displayed, it is possible to reduce the variation in the visual evaluation due to the individual difference of the radiologist.

In addition, in a case in which the image quality is adjusted, since the ES image quality can be quickly adjusted only by the operation of changing the ES level value by clicking or the like, the load of the adjustment of the image quality can be reduced, and the ES image quality can be quickly adjusted even during the imaging. Therefore, the radiologist who is the user can handle the processing of a large amount of radiation images, and can reduce a frequency of reimaging due to an imaging failure or the like.

As described above, with the processing apparatus 10, the load for checking the image quality by the radiologist can be reduced by quantifying and indicating the ES image quality. In addition, it is possible to reduce the variation in the visual evaluation due to the individual difference of the radiologist. In addition, since the ES image quality indicator is related to the generation of the ES image and the ES image quality can be adjusted only by the operation of changing the ES level value, the image quality can be adjusted more easily and reliably. Therefore, with the processing apparatus 10, the ES image having a better image quality can be easily and quickly generated. Therefore, with the processing apparatus 10 or the like, the load for checking the image quality of the ES image by the radiologist during the imaging is also greatly reduced.

Figure 11:
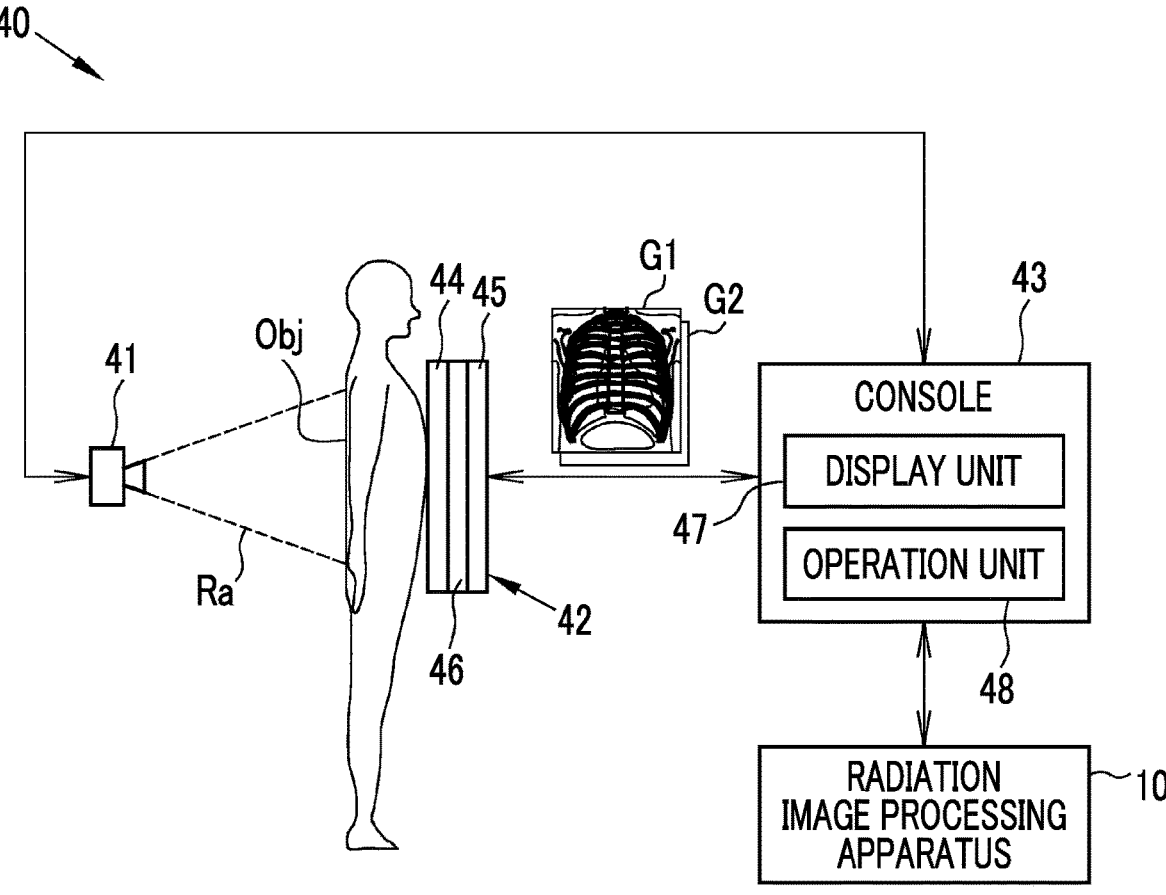
FIG. 11 is a schematic diagram of a radiography system.

Hereinafter, an example of an embodiment of a radiography system or the like including the processing apparatus 10 will be described. As shown in FIG. 11, the radiography system 40 according to the present embodiment comprises a radiation source 41, a radiography panel 42, a console 43, and the processing apparatus 10. The radiation source 41, the radiography panel 42, and the console 43 configure the radiography apparatus.

The radiography apparatus can image the entire specific subject. Therefore, the radiography apparatus is configured by the radiation source 41, the radiography panel 42, and the like that can image the entire chest of the person who is the specific subject.

The radiation source 41 is a device that generates radiation Ra required for the imaging, and consists of a radiation tube that generates the radiation Ra, a high voltage generation circuit that generates a high voltage required for the radiation tube to generate the radiation Ra, and the like. The radiation source 41 can generate a plurality of types of radiation having different radiation qualities (energy distribution (hereinafter, simply referred to as energy)) by adjusting the tube voltage, the tube current, and the like of the radiation tube. In the present embodiment, the radiation source 41 is an X-ray source that generates X-rays. Therefore, the radiography system 40 is an X-ray imaging system that acquires an X-ray image of a subject Obj by imaging the subject Obj using the X-rays. The subject Obj is, for example, a person, and in the present embodiment, the chest of the person is imaged as the specific subject Obj.

The radiography panel 42 images the subject Obj using the radiation Ra generated by the radiation source 41. That is, the radiography panel 42 is a so-called flat panel detector (FPD), and outputs a radiation image of the subject Obj by detecting the radiation Ra transmitted through the subject Obj and converting the radiation Ra into an electric signal. In the imaging using the radiography panel 42, a grid (not shown) can be used in combination as required. The grid is a device that removes scattered ray components of the radiation, and is, for example, a static Lysholm grid, a moving Bucky grid, or the like.

In the present embodiment, the radiography panel 42 comprises two detectors of a first radiation detector 44 and a second radiation detector 45. Out of the first radiation detector 44 and the second radiation detector 45, a detector that is disposed relatively close to the subject Obj and the radiation source 41 is the first radiation detector 44, and a detector that is disposed relatively far from the subject Obj and the radiation source 41 is the second radiation detector 45. The first radiation detector 44 and the second radiation detector 45 detect the radiation Ra transmitted through the subject Obj for each pixel. In addition, the first radiation detector 44 and the second radiation detector 45 output the radiation images of the subject Obj, respectively.

The radiography panel 42 comprises a radiation energy conversion filter 46 between the first radiation detector 44 and the second radiation detector 45. The radiation energy conversion filter 46 is, for example, a copper plate or the like, and absorbs a low energy component of the radiation Ra. Therefore, the energy of the radiation Ra is changed after being transmitted through the first radiation detector 44 and before reaching the second radiation detector 45. Therefore, the radiography panel 42 simultaneously images the specific subject Obj under the same imaging condition (same radiation Ra), but the first radiation image G1 (see FIG. 1) output by the first radiation detector 44 and the second radiation image G2 (see FIG. 1) output by the second radiation detector 45 are the radiation images in which the specific subject is imaged by respectively using energies of the two types of the radiation Ra that are substantially different from each other. It should be noted that this method may be called 1-shot energy subtraction (1-shot ES).

It should be noted that the first radiation detector 44 and the second radiation detector 45 may be either an indirect conversion type detector or a direct conversion type detector, and different types of detectors can be adopted in the first radiation detector 44 and the second radiation detector 45. The indirect conversion type detector is a detector that indirectly obtains an electric signal by converting the radiation Ra into visible light using a scintillator consisting of cesium iodide (CsI) or the like and photoelectrically converting the visible light. The direct conversion type detector is a detector that directly converts the radiation Ra into an electric signal using a scintillator consisting of amorphous selenium or the like. In addition, each of the first radiation detector 44 and the second radiation detector 45 may be a penetration side sampling (PSS) system detector or an irradiation side sampling (ISS) system detector. The PSS system is a system in which a scintillator is disposed on the subject Obj side with respect to a thin film transistor (TFT) that reads out an electric signal. Contrary to the PSS system, the ISS system is a system in which a scintillator and a TFT are disposed in the order of the TFT and the scintillator from the subject Obj side.

In addition, in a case in which the radiation source 41 generates two or more types of radiation having different radiation qualities by adjusting the tube voltage, the tube current, and the like of the radiation tube, the radiography panel 42 comprises at least one radiation detector. In this case, the radiation detector can be the same as the first radiation detector 44, the second radiation detector 45, or the like.

In this case, the radiography panel 42 images the specific subject Obj at least twice using the respective radiation qualities under the same imaging condition except that the radiation qualities are different. The first radiation image G1 (see FIG. 1) output by the first radiation detector and the second radiation image G2 (see FIG. 1) output by the second radiation detector are the radiation images in which the specific subject is imaged by respectively using energies of the two types of the radiation Ra that are different from each other. It should be noted that this method may be called 2-shot energy subtraction (2-shot ES).

Figure 12:
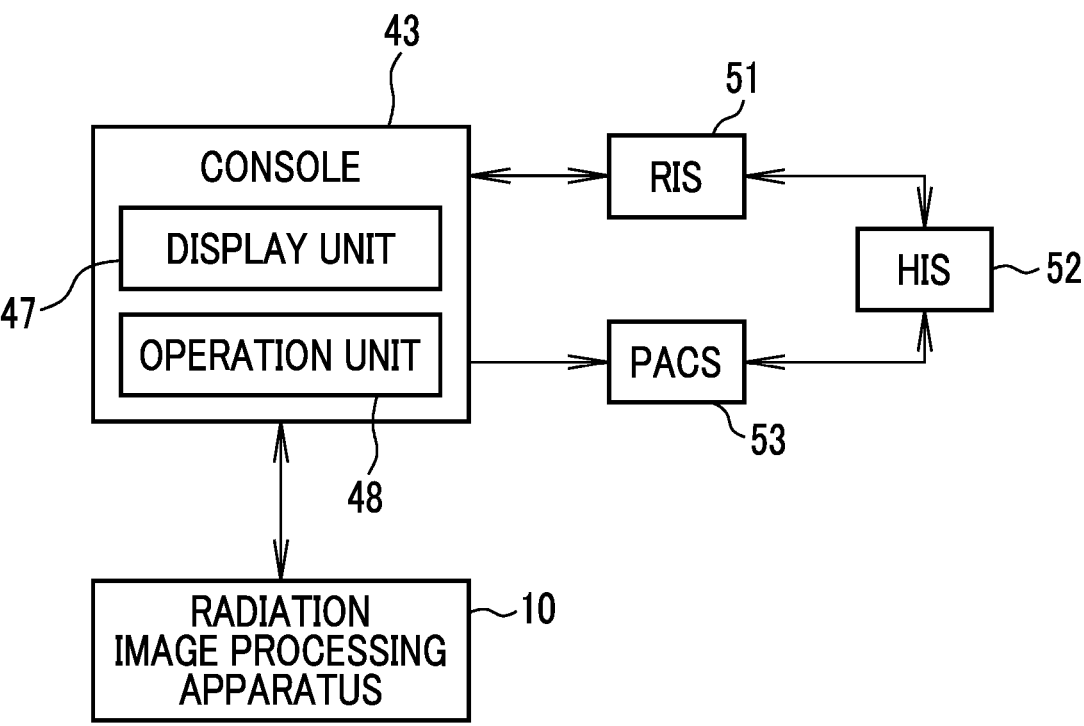
FIG. 12 is an explanatory diagram describing a function and a connection apparatus of a console.

The console 43 is a control device (computer) that controls the operations of the radiation source 41, the radiography panel 42, and the like, and is, for example, a computer, such as a personal computer or a workstation, in which an application program for realizing a predetermined function is installed. As shown in FIG. 12, the console 43 may be connected to radiology information systems (RIS) 51, hospital information systems (HIS) 52, picture archiving and communication systems (PACS) 53, or a digital imaging and communications in medicine (DICOM) server (not shown) provided in the PACS 53, and acquires imaging information, such as an imaging order related to the imaging of the radiation image from these systems, and transmits the captured image.

The console 43 comprises a display unit 47 and an operation unit 48. The display unit 47 is, for example, a liquid crystal display, and performs displaying of the captured radiation image or other required displaying related to the operation, the setting, or the like. The operation unit 48 is, for example, a keyboard and/or a pointing device used for setting input of the imaging condition and the like and operating the radiation source 41 and the radiography panel 42. The display unit 47 and the operation unit 48 can be configured with a touch panel.

In the present embodiment, the processing apparatus 10 is an apparatus separate from the console 43, but a part or entirety of the processing apparatus 10 can be provided on the console 43. In this case, the display unit 47 and/or the operation unit 48 of the console 43 can be used as the display unit 16 and/or the operation unit 17 of the processing apparatus 10. In addition, in a case in which the entirety of the processing apparatus 10 is provided in the console 43, the console 43 configures the processing apparatus 10.

As described above, the processing apparatus 10 comprises the image acquisition unit 11, the image processing unit 12, the correlation information generation unit 13, the display controller 14, the change reception unit 15, the display unit 16, and the operation unit 17 (see FIG. 1). The display unit 16 may be shared with the display unit 47 of the console 43. The processing apparatus 10 stores programs related to various types of processing in a program memory (not shown). In the processing apparatus 10, the functions of the image acquisition unit 11, the image processing unit 12, the correlation information generation unit 13, the display controller 14, the change reception unit 15, the display unit 16, the operation unit 17, a central control unit, and the like are realized by operating the programs in the program memory by the central control unit (not shown) configured by the processor or the like.

The processing apparatus 10 is directly connected to the console 43, and the image acquisition unit 11 can acquire the captured radiation image of the subject Obj in real time and use the acquired radiation image for the image processing. It should be noted that, in addition to being directly connected to the console 43, the processing apparatus 10 may indirectly acquire the radiation image via the RIS 51, the HIS 52, the PACS 53, or the DICOM server (not shown) provided in the PACS 53 and use the acquired radiation image for the image processing. In addition, the processing apparatus 10 may transmit and store the processing image, such as the bone part image Gb or the soft part image Gt adjusted by the processing apparatus 10, to an external device such as the DICOM server, together with the image being adjusted.

Figure 13:
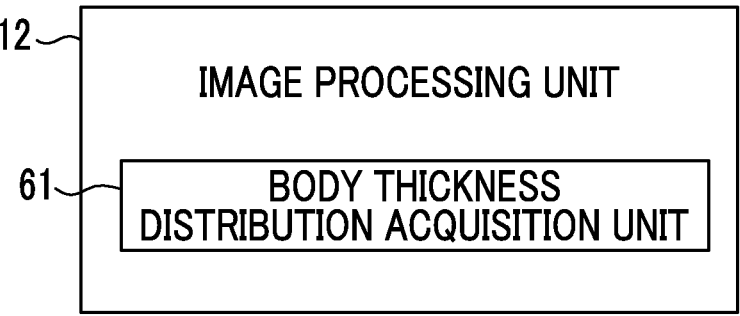
FIG. 13 is a block diagram showing a function of an image processing unit.

It should be noted that, as described above, in a case in which the scattered ray correction processing is performed, the image processing unit 12 may comprise a body thickness distribution acquisition unit 61 as shown in FIG. 13. Since the body thickness distribution of the subject Obj may be either of a measurement value or an estimation value, the body thickness distribution acquisition unit 61 acquires a measurement value of the body thickness distribution of the subject Obj or acquires an estimation value of the body thickness distribution of the subject Obj. The body thickness distribution acquisition unit 61 estimates the scattered rays for each pixel of a correction target image to be corrected based on the acquired body thickness distribution, and removes the scattered rays from each pixel of the correction target image. For the correction target image in which the removal of the scattered rays is completed, the subsequent processing is recommended.

It should be noted that, in the present embodiment, all the correction target images are images in which the specific subject is imaged, and the first radiation image G1 and the second radiation image G2 are radiation images obtained substantially simultaneously by the so-called 1-shot ES method. Therefore, the body thickness distribution of the subject Obj can be estimated based on any one of the correction target images, and the obtained estimation value can be used as it is as the body thickness distribution of all the correction target images.

Figure 14:
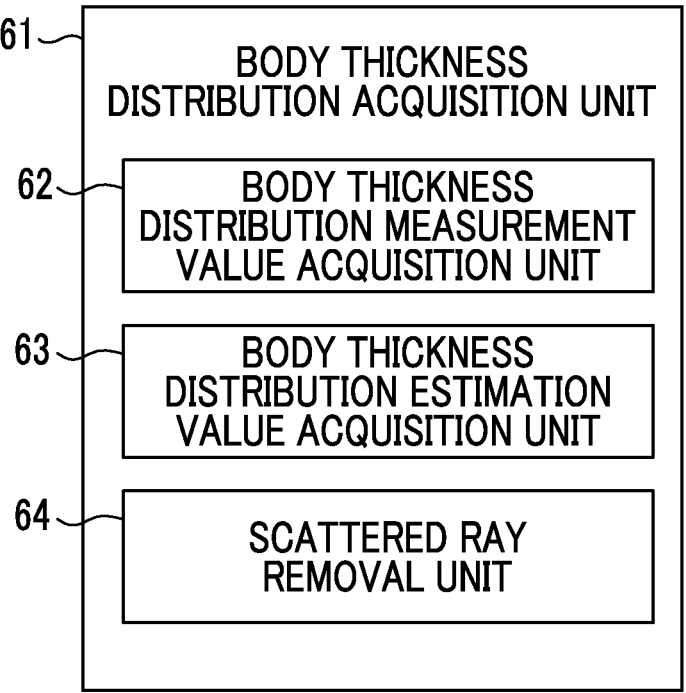
FIG. 14 is a block diagram showing a function of a body thickness distribution acquisition unit.

As shown in FIG. 14, the body thickness distribution acquisition unit 61 comprises a body thickness distribution measurement value acquisition unit 62, a body thickness distribution estimation value acquisition unit 63, and a scattered ray removal unit 64. The body thickness distribution measurement value acquisition unit 62 acquires the measured body thickness distribution. The body thickness distribution measurement value acquisition unit 62 acquires a measurement value obtained by actually measuring the body thickness distribution, and sets the measurement value as the body thickness distribution of the subject Obj.

The body thickness distribution measurement value acquisition unit 62 calculates the body thickness distribution T(x, y) of the subject H based on the source image receptor distance (SID) and a source object distance (SOD) included in the imaging condition. It is preferable that the SOD is acquired by, for example, a time of flight (TOF) camera. It is preferable that the SID is acquired by, for example, a potentiometer, an ultrasound range finder, a laser range finder, or the like.

It is preferable that the body thickness distribution is obtained by subtracting the SOD from the SID. Also, the body thickness distribution is calculated for each pixel corresponding to the first and second radiation images G1 and G2. It should be noted that, instead of calculating the body thickness distribution based on the SID and the SOD, the body thickness distribution may be calculated from at least any one of the first radiation image G1 or the second radiation image G2. In addition, the body thickness distribution may be calculated from the soft part image of the subject Obj obtained by performing the weighting subtraction between the respective corresponding pixels of the first radiation image G1 and the second radiation image G2. It should be noted that, in a case in which the body thickness distribution is obtained, in a case in which the first and second radiation detectors 44 and 45 are provided in an imaging table (not shown) on which the subject Obj is placed, it is preferable that a distance between the radiation source 41 and a surface of the imaging table on which the subject Obj is in contact is used as the SID.

The body thickness distribution estimation value acquisition unit 63 acquires the estimation value of the body thickness distribution of the subject by using a known method. As a method of acquiring the estimation value of the body thickness distribution or performing the image processing of removing the scattered rays using the acquired estimation value of the body thickness distribution, for example, a method using a virtual model disclosed in JP2015-043959A can also be adopted, in addition to the method using the LUT 20 (FIG. 5).

In the method using the virtual model, first, the virtual model having a predetermined body thickness distribution is acquired, and an estimation primary ray image and an estimation scattered ray image obtained by radiography of the virtual model are combined to generate an estimation image. Next, the body thickness distribution of the virtual model is modified such that an error value indicating a difference between the pixel values of the pixels at the respective corresponding positions is small from a subject image obtained by radiography of the subject Obj and the estimation image. The body thickness distribution of the modified virtual model is decided as the body thickness distribution of the subject. In this way, for example, even in the subject imaged without using the grid, the influence of the scattered rays can be suppressed, and a more accurate estimation value of the body thickness distribution can be obtained. The acquired body thickness distribution is used in the contrast correction processing, the scattered ray correction processing, and the like.

It is preferable that the scattered ray removal unit 64 generates the bone part image Gb or the soft part image Gt by removing the scattered rays from the first radiation image G1 or the second radiation image G2 by the scattered ray correction processing and then performing the image processing, such as the bone part extraction or the soft part extraction, by using the acquired body thickness distribution. Since various types of image processing is performed while suppressing the influence of the scattered rays by the scattered ray correction processing, it is possible to generate the bone part image Gb or the soft part image Gt having a better image quality.

It should be noted that the display controller 14 performs control of displaying, on the display unit 16, the first emphasis image, the level value, and the image quality indicator, but it is preferable that the display controller 14 performs control of setting the specific range in the image quality indicator as the reference range, and displaying, on the display unit 16, the image quality indicator and the reference range. The specific range to be set as the reference range can be set in advance. In the reference range, for example, in a case in which the ES image quality indicator is within the reference range, since the image quality of the ES image is sufficiently good, a range of the ES image quality indicator in a case in which the adjustment of the image quality is not further required can be set as the reference range. In addition, it is possible to grasp at a glance whether or not the ES image quality of the ES image is within a certain reference by setting the reference range.

Figure 15:
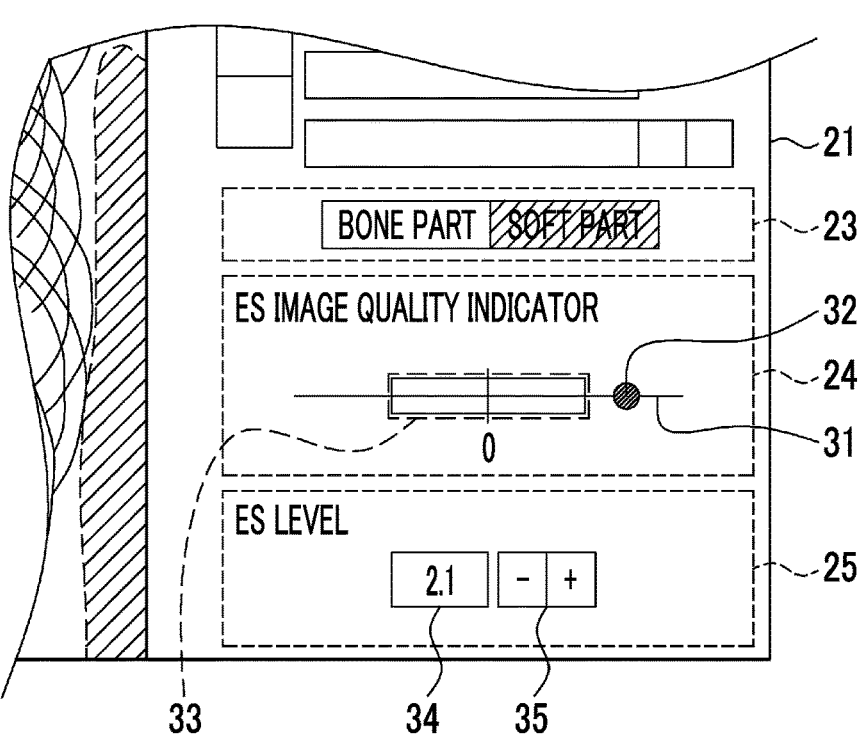
FIG. 15 is an explanatory diagram describing display of the image quality indicator and the ES level value of the ES image showing a reference range before the ES level value is changed.

As shown in FIG. 15, in the present embodiment, the reference range on the number line 31 is indicated by a rectangle 33 as the specific range centered on the scale of 0. In a case in which the point 32 indicating the ES image quality indicator of the bone part image Gb displayed on the screen 21 is not inside the rectangle 33 indicating the reference range, the ES image quality of the bone part image Gb displayed on the screen 21 is outside the reference range, and it is required to adjust the ES image quality such that the ES image quality indicator is improved. Therefore, it can be seen at a glance whether or not adjustment of the ES image quality or the like is required for the bone part image Gb displayed on the screen 21.

Figure 16:
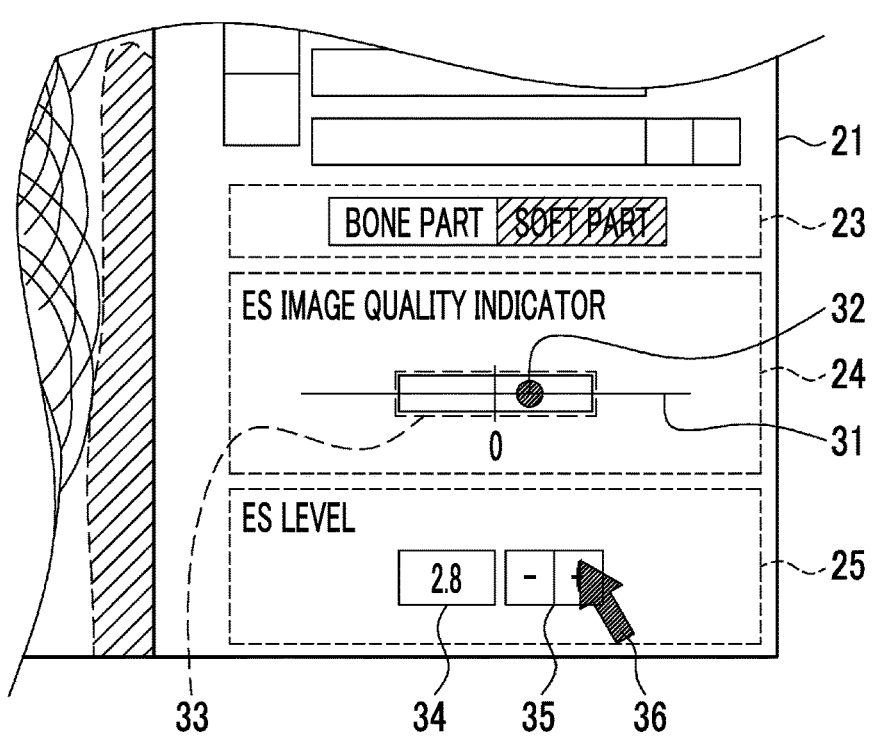
FIG. 16 is an explanatory diagram describing display of the image quality indicator and the ES level value of the ES image showing the reference range after the ES level value is changed.

As shown in FIG. 15, in a case in which the image quality indicator of the generated first emphasis image is out of the reference range, the user can repeat the change of the ES level value a plurality of times to generate the first emphasis image with improved ES image quality. In addition, as shown in FIG. 16, in a case in which the image quality indicator of the generated first emphasis image is within the reference range, it can be seen at a glance that the adjustment of the image quality is not required.

As described above, by setting the specific range of the image quality indicator as the reference range and displaying the specific range on the display, it is possible to grasp at a glance whether or not the image quality of each of the ES images is equal to or higher than a certain reference. In addition, even in a case in which the image quality does not meet the certain reference, the change of the ES level value may be repeated a plurality of times, and the changed ES image quality indicator is displayed each time, so that it is possible to know of how much the ES image quality indicator is to be improved or deteriorated by converting the numerical value. Therefore, it is possible to easily and quickly perform the adjustment of the ES image quality to be within the reference range.

Figure 17:
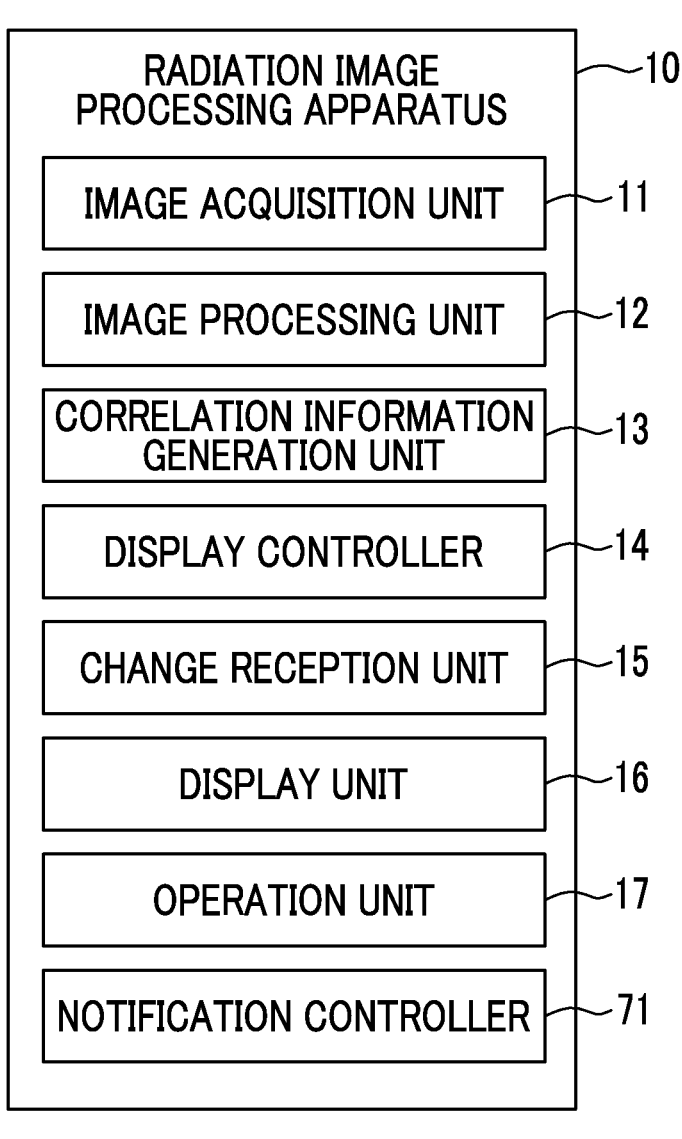
FIG. 17 is a block diagram describing a function of the radiation image processing apparatus comprising a notification controller.

In addition, the processing apparatus 10 may give a notification to the user in a case in which the image quality indicator is not included in the reference range. In this case, as shown in FIG. 17, the processing apparatus 10 comprises a notification controller 71. The notification need only be provided in an aspect in which, in a case in which the image quality indicator is not included in the reference range, the user can understand that fact, and any aspect may be adopted, such as a notification by display on the display, a notification by sound, and/or a notification by vibration of a mobile device that communicates with the processing apparatus 10.

Figure 18:
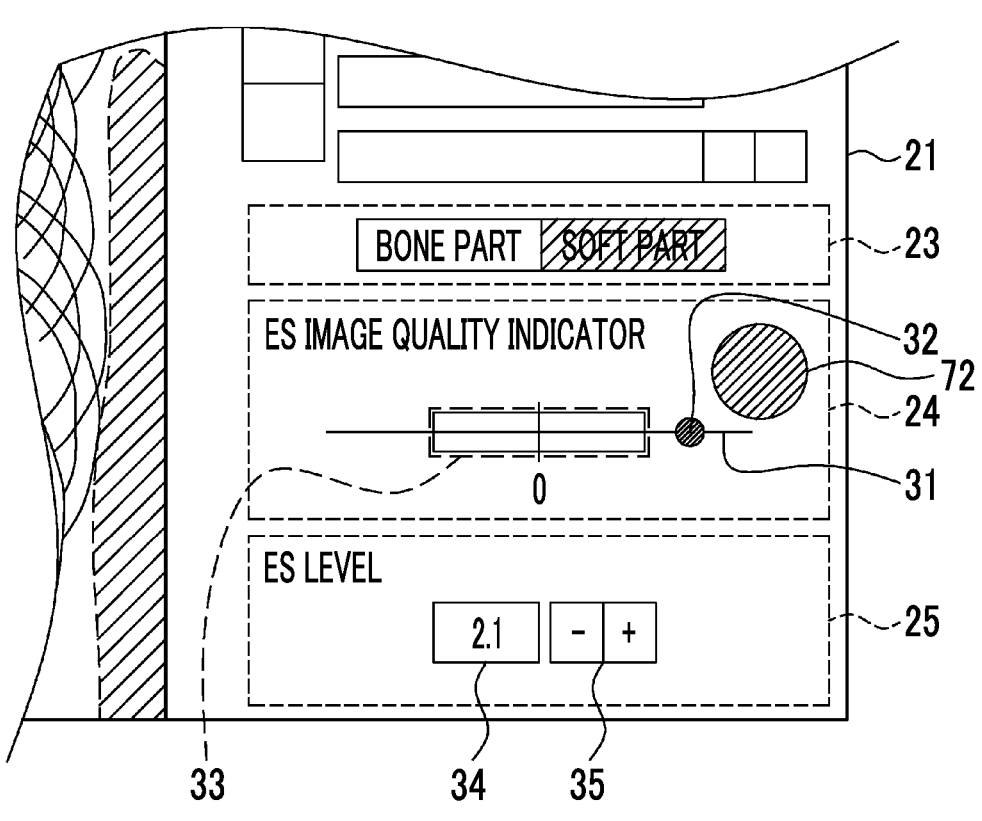
FIG. 18 is an explanatory diagram describing warning display.

In the present embodiment, the notification is given by displaying on the display unit 16. As shown in FIG. 18, for example, in a case in which the image quality indicator is out of the reference range for the generated first emphasis image in a case in which the ES image quality indicator is displayed, warning display 72 can be displayed or turned on and off on the ES image quality indicator display unit 24. In addition, the background color of the entire ES image quality indicator display unit 24 may be displayed in a color different from the normal color. As a result, the radiologist who is the user can recognize that the ES image currently displayed on the display is required to be further adjusted even in a case in which the radiologist does not pay particular attention to the display unit 16.

As described above, by giving the notification to the radiologist in a case in which the image quality indicator is not included in the reference range, the radiologist can recognize that the ES image quality indicator is not included in the reference range and the adjustment is required, even in a case in which the radiologist does not pay particular attention to the display unit 16. Therefore, it is particularly effective in a case in which the user has to generate a large number of the ES images.

In addition, in the embodiment described above, the radiation image in which the chest of the person is the specific subject is used, but any specific subject may be used as long as the image is the ES image, and other parts of a person or an animal, a tissue, such as a blood vessel, can also be applied as the specific subject. In addition, since the ES image can also be used to view the temporal change, the ES image can also be applied to the ES image for viewing the temporal change. Therefore, the specific subject can also be architecture, such as a pipe or a crack of a structure, in addition to the person or the animal.

In addition, in the embodiment described above, the first emphasis image or the second emphasis image is the image generated based on the acquired radiation image, but may be an image for which the adjustment of the image quality is completed by the processing apparatus 10. For example, in a case of generating the first emphasis image, the second emphasis image for which the adjustment of the image quality is completed by the processing apparatus 10 may be used. As a result, it is possible to obtain the ES image having a further improved image quality.

In the embodiment described above, a hardware structure of processing units, such as the image acquisition unit 11, the image processing unit 12, the correlation information generation unit 13, the display controller 14, the change reception unit 15, the notification controller 71, or the central control unit (not shown) provided in the processing apparatus 10, or the central control unit (not shown) provided in the console 43, is various processors as described below. Examples of the various processors include a central processing unit (CPU), which is a general-purpose processor that executes software (program) to function as various processing units, a programmable logic device (PLD), which is a processor of which a circuit configuration can be changed after manufacturing, such as a field programmable gate array (FPGA), and a dedicated electric circuit, which is a processor of which a circuit configuration is designed exclusively for executing various pieces of processing.

One processing unit may be configured by one of these various processors, or may be configured by a combination of two or more same type or different type of processors (for example, a plurality of FPGAs, or a combination of a CPU and an FPGA). Moreover, a plurality of processing units may be configured by one processor. As an example in which the plurality of processing units are configured by one processor, first, there is a form in which one processor is configured by a combination of one or more CPUs and software, and this processor functions as the plurality of processing units, as represented by a computer, such as a client or a server. Second, as represented by a system on chip (SoC) or the like, there is a form of using a processor that realizes the functions of the entire system including the plurality of processing units with one integrated circuit (IC) chip. As described above, various processing units are configured by one or more of the various processors described above, as the hardware structure.

More specifically, the hardware structure of these various processors is an electric circuit (circuitry) having a form in which circuit elements, such as semiconductor elements, are combined.

From the above description, the radiation image processing apparatus according to the following Supplementary Notes 1 to 16 can be grasped.

Supplementary Note 1

A radiation image processing apparatus comprising a processor, in which the processor acquires two radiation images in which a specific subject is imaged by respectively using two types of radiation energies different from each other, generates a first emphasis image by performing first emphasis processing on the two radiation images using an arithmetic expression including a first parameter, generates a second emphasis image by performing second emphasis processing using at least any radiation image of the two radiation images, generates correlation information indicating a correlation between the first emphasis image and the second emphasis image, performs control of displaying, on a display unit, the first emphasis image, a level value corresponding to a value of the first parameter, and an image quality indicator indicating a degree of difference between the first emphasis image and the second emphasis image, which is quantified based on the correlation information, and receives a change of the level value.

Supplementary Note 2

The radiation image processing apparatus according to Supplementary Note 1, in which the processor updates the value of the first parameter in a case in which the change of the level value is received, generates the first emphasis image by using the updated value of the first parameter, and displays, on the display unit, the level value updated corresponding to the updated value of the first parameter.

Supplementary Note 3

The radiation image processing apparatus according to Supplementary Note 1 or 2, in which the processor performs control of displaying, on the display unit, a user interface that receives the change of the level value by a user.

Supplementary Note 4

The radiation image processing apparatus according to any one of Supplementary Notes 1 to 3, in which, in the radiation image, a scattered ray component estimated according to a body thickness of the subject is removed for each pixel.

Supplementary Note 5

The radiation image processing apparatus according to any one of Supplementary Notes 1 to 4, in which the first emphasis processing is subtraction processing.

Supplementary Note 6

The radiation image processing apparatus according to any one of Supplementary Notes 1 to 5, in which the subject includes a bone part and a soft part, and the first emphasis image is a bone part image, and the second emphasis image is a soft part image.

Supplementary Note 7

The radiation image processing apparatus according to any one of Supplementary Notes 1 to 5, in which the subject includes a bone part and a soft part, and the first emphasis image is a soft part image, and the second emphasis image is a bone part image.

Supplementary Note 8

The radiation image processing apparatus according to any one of Supplementary Notes 1 to 7, in which the first emphasis processing includes processing of weighting one radiation image of the two radiation images by using the first parameter, and then subtracting the weighted radiation image from the other radiation image.

Supplementary Note 9

The radiation image processing apparatus according to any one of Supplementary Notes 1 to 8, in which the second emphasis processing includes processing of weighting one radiation image of the two radiation images by using a second parameter, and then subtracting the weighted radiation image from the other radiation image.

Supplementary Note 10

The radiation image processing apparatus according to any one of Supplementary Notes 1 to 5, in which the subject includes a bone part and a soft part, the first emphasis image is a bone part image, and the second emphasis image is a soft part image, and in a case in which a pixel value at coordinates (x, y) in one radiation image of the two radiation images is $G1(x, y)$, a pixel value at coordinates (x, y) in the other radiation image is $G2(x, y)$, a pixel value at coordinates (x, y) in the bone part image is Gb(x, y), a pixel value at coordinates (x, y) in the soft part image is Gt(x, y), the first parameter is $\alpha$, and a second parameter is $\beta$, the bone part image is generated by Expression (1), and the soft part image is generated by Expression (4).

$$Gb(x,y)=G1(x,y)-\alpha \times G2(x,y) \qquad (1)$$

$$Gt(x,y)=G1(x,y)-\beta \times G2(x,y) \qquad (4)$$

Supplementary Note 11

The radiation image processing apparatus according to any one of Supplementary Notes 1 to 8, in which the second emphasis processing is processing of subtracting the first emphasis image from any radiation image of the two radiation images.

Supplementary Note 12

The radiation image processing apparatus according to any one of Supplementary Notes 1 to 5, in which the subject includes a bone part and a soft part, the first emphasis image is a bone part image, and the second emphasis image is a soft part image, and in a case in which a pixel value at coordinates (x, y) in one radiation image of the two radiation images is $G1(x, y)$, a pixel value at coordinates (x, y) in the other radiation image is $G2(x, y)$, a pixel value at coordinates (x, y) in the bone part image is Gb(x, y), a pixel value at coordinates (x, y) in the soft part image is Gt(x, y), and the first parameter is $\alpha$, the bone part image is generated by Expression (1), and the soft part image is generated by Expression (2) or (3).

$$Gb(x,y)=G1(x,y)-\alpha \times G2(x,y) \qquad (1)$$

$$Gt(x,y)=G1(x,y)-Gb(x,y) \qquad (2)$$

$$Gt(x,y)=G2(x,y)-Gb(x,y) \qquad (3)$$

Supplementary Note 13

The radiation image processing apparatus according to any one of Supplementary Notes 1 to 12, in which the correlation information is a correlation coefficient between a pixel value of the first emphasis image and a pixel value of the second emphasis image.

Supplementary Note 14

The radiation image processing apparatus according to Supplementary Note 13, in which the image quality indicator is the correlation coefficient.

Supplementary Note 15

The radiation image processing apparatus according to any one of Supplementary Notes 1 to 14, in which the processor performs control of setting a specific range in the image quality indicator as a reference range, and displaying, on the display unit, the image quality indicator and the reference range.

Supplementary Note 16

The radiation image processing apparatus according to Supplementary Note 15, in which the processor performs control of giving a notification to a user in a case in which the image quality indicator is not included in the reference range.

EXPLANATION OF REFERENCES

10: radiation image processing apparatus
11: image acquisition unit
12: image processing unit
13: correlation information generation unit
14: display controller
15: change reception unit
16: display unit
17: operation unit
20: LUT
21: screen
22: image adjustment unit
23: ES image switching unit
24: ES image quality indicator display unit
25: ES level display unit
31: number line
32: point
33: rectangle
34: ES level value display unit
35: ES level value change unit
36: cursor
40: radiography system
41: radiation source
42: radiography panel
43: console
44: first radiation detector
45: second radiation detector
46: radiation energy conversion filter
47: display unit
48: operation unit
51: RIS
52: HIS
53: PACS
61: body thickness distribution acquisition unit
62: body thickness distribution measurement value acquisition unit
63: body thickness distribution estimation value acquisition unit
64: scattered ray removal unit
71: notification controller
72: warning display
G1: first radiation image
G2: second radiation image
Gb: bone part image
Gt: soft part image
Obj: subject
Ra: X-rays
ST110 to ST180: step

What is claimed is:

1. A radiation image processing apparatus comprising:
a processor, configured to:
    acquire two radiation images in which a specific subject is imaged by respectively using two types of radiation energies different from each other;
    generate a first emphasis image by performing first emphasis processing on the two radiation images using an arithmetic expression including a first parameter;
    generate a second emphasis image by performing second emphasis processing using at least any radiation image of the two radiation images;
    generate correlation information indicating a correlation between the first emphasis image and the second emphasis image;
    perform control of displaying, on a display unit, the first emphasis image, a level value corresponding to a value of the first parameter, and an image quality indicator indicating a degree of difference between the first emphasis image and the second emphasis image, which is quantified based on the correlation information; and
    receive a change of the level value,
wherein the subject includes a bone part and a soft part, and a combination of the first emphasis image and the second emphasis image is one of the following:
    the first emphasis image is a bone image, and the second emphasis image is a soft part image; or
    the first emphasis image is the soft part image, and the second emphasis image is the bone image.

2. The radiation image processing apparatus according to claim 1,
wherein the processor is configured to:
    update the value of the first parameter in a case in which the change of the level value is received;
    generate the first emphasis image by using the updated value of the first parameter; and
    display, on the display unit, the level value updated corresponding to the updated value of the first parameter.

3. The radiation image processing apparatus according to claim 1,
wherein the processor is configured to perform control of displaying, on the display unit, a user interface that receives the change of the level value by a user.

4. The radiation image processing apparatus according to claim 1,
wherein, in the radiation image, a scattered ray component estimated according to a body thickness of the subject is removed for each pixel.

5. The radiation image processing apparatus according to claim 1,
wherein the first emphasis processing is subtraction processing.

6. The radiation image processing apparatus according to claim 1,
wherein the first emphasis processing includes processing of weighting one radiation image of the two radiation images by using the first parameter, and then subtracting the weighted radiation image from the other radiation image.

7. The radiation image processing apparatus according to claim 1,
wherein the second emphasis processing includes processing of weighting one radiation image of the two radiation images by using a second parameter, and then subtracting the weighted radiation image from the other radiation image.

8. The radiation image processing apparatus according to claim 1, wherein the subject includes a bone part and a soft part, the first emphasis image is a bone part image, and the second emphasis image is a soft part image, and in a case in which a pixel value at coordinates (x, y) in one radiation image of the two radiation images is G1(x, y), a pixel value at coordinates (x, y) in the other radiation image is G2(x, y), a pixel value at coordinates (x, y) in the bone part image is Gb (x, y), a pixel value at coordinates (x, y) in the soft part image is Gt (x, y), the first parameter is α, and a second parameter is β, the bone part image is generated by Expression (1), and the soft part image is generated by Expression (4)

$$Gb(x,y)=G1(x,y)-\alpha \times G2(x,y) \quad (1)$$

$$Gt(x,y)=G1(x,y)-\beta \times G2(x,y) \quad (4).$$

9. The radiation image processing apparatus according to claim 1, wherein the second emphasis processing is processing of subtracting the first emphasis image from any radiation image of the two radiation images.

10. The radiation image processing apparatus according to claim 1, wherein the subject includes a bone part and a soft part, the first emphasis image is a bone part image, and the second emphasis image is a soft part image, and in a case in which a pixel value at coordinates (x, y) in one radiation image of the two radiation images is G1(x, y), a pixel value at coordinates (x, y) in the other radiation image is G2(x, y), a pixel value at coordinates (x, y) in the bone part image is Gb (x, y), a pixel value at coordinates (x, y) in the soft part image is Gt (x, y), and the first parameter is α, the bone part image is generated by Expression (1), and the soft part image is generated by Expression (2) or (3)

$$Gb(x,y)=G1(x,y)-\alpha \times G2(x,y) \quad (1)$$

$$Gt(x,y)=G1(x,y)-Gb(x,y) \quad (2)$$

$$Gt(x,y)=G2(x,y)-Gb(x,y) \quad (3).$$

11. The radiation image processing apparatus according to claim 1, wherein the correlation information is a correlation coefficient between a pixel value of the first emphasis image and a pixel value of the second emphasis image.

12. The radiation image processing apparatus according to claim 11, wherein the image quality indicator is the correlation coefficient.

13. The radiation image processing apparatus according to claim 1, wherein the processor is configured to perform control of setting a specific range in the image quality indicator as a reference range, and displaying, on the display unit, the image quality indicator and the reference range.

14. The radiation image processing apparatus according to claim 13, wherein the processor is configured to perform control of giving a notification to a user in a case in which the image quality indicator is not in the reference range.

15. An operation method of a radiation image processing apparatus, the method comprising:

a step of acquiring two radiation images in which a specific subject is imaged by respectively using two types of radiation energies different from each other;

a step of generating a first emphasis image by performing first emphasis processing on the two radiation images using an arithmetic expression including a first parameter;

a step of generating a second emphasis image by performing second emphasis processing using at least any radiation image of the two radiation images;

a step of generating correlation information indicating a correlation between the first emphasis image and the second emphasis image; and a step of performing control of displaying, on a display unit, the first emphasis image, a level value corresponding to a value of the first parameter, and an image quality indicator indicating a degree of difference between the first emphasis image and the second emphasis image, which is quantified based on the correlation information, wherein the subject includes a bone part and a soft part, and a combination of the first emphasis image and the second emphasis image is one of the following:

the first emphasis image is a bone image, and the second emphasis image is a soft part image; or the first emphasis image is the soft part image, and the second emphasis image is the bone image.

16. A non-transitory computer readable medium for storing a computer-executable program for causing a computer to function as a radiation image processing apparatus, the computer-executable program causing the computer to execute:

a function of acquiring two radiation images in which a specific subject is imaged by respectively using two types of radiation energies different from each other;

a function of generating a first emphasis image by performing first emphasis processing on the two radiation images using an arithmetic expression including a first parameter;

a function of generating a second emphasis image by performing second emphasis processing using at least any radiation image of the two radiation images;

a function of generating correlation information indicating a correlation between the first emphasis image and the second emphasis image; and a function of performing control of displaying, on a display unit, the first emphasis image, a level value corresponding to a value of the first parameter, and an image quality indicator indicating a degree of difference between the first emphasis image and the second emphasis image, which is quantified based on the correlation information, wherein the subject includes a bone part and a soft part, and a combination of the first emphasis image and the second emphasis image is one of the following:

the first emphasis image is a bone image, and the second emphasis image is a soft part image; or the first emphasis image is the soft part image, and the second emphasis image is the bone image.

* * * * *